United States Patent [19]
Chen et al.

[11] Patent Number: 5,821,052
[45] Date of Patent: Oct. 13, 1998

[54] CONTROL OF THE SYNTHESIS OF PROTEINS BY ANITISENSE RNA-TRNA COMPLEX

[75] Inventors: Gia-fen T. Chen, South Plainfield; Oleg Mirochnitchenko, Highland Park; Masayori Inouye, Bridgewater, all of N.J.

[73] Assignee: University of Medicine and Dentistry of New Jersey, Newark, N.J.

[21] Appl. No.: 345,623

[22] Filed: Nov. 28, 1994

Related U.S. Application Data

[63] Continuation-in-part of Ser. No. 869,766, Apr. 16, 1992, abandoned.

[51] Int. Cl.$^6$ .......................... C12H 21/00; C12N 15/63; C12Q 1/02; C12Q 1/68
[52] U.S. Cl. .................................. 435/6; 435/29; 435/32; 435/172.3; 435/252.3; 435/320.1; 536/24.5
[58] Field of Search ........................ 435/6, 172.1, 172.3, 435/252.3, 252.33, 320.1, 69.1, 71.2, 29, 32; 514/44; 536/23.1, 24.1, 24.5; 800/33, 44

[56] References Cited

U.S. PATENT DOCUMENTS

| | | | |
|---|---|---|---|
| 5,245,022 | 9/1993 | Weis et al. | 536/24.5 |
| 5,585,479 | 12/1996 | Hoke et al. | 536/24.5 |

OTHER PUBLICATIONS

Nakajima et al. "Organization and structure of an *E. coli* tRNA Operon . . . " Cell 23:239–249, Jan. 1991.

Norrander et al. "Construction of improved M13 vectors . . . " Gene 26:101–106, 1983.

Gewirtz et al. "Facilitating oligonucleoitde delivery: Helping antisnese deliver on its promise" Proc. Natl. acad. Sci. USA 93: 3161–3163, Apr. 1996.

Rojanasakul "Antisense oligonucleotide theraputics: Drug delivery and targeting" Adv. Drug Delivery Rev. 18: 116–131, 1996.

Oleg Mirochnitchenko and Masayori Inouye, "Evaluation of the Use of Antisense tRNA$^{met}$ as an Inhibitor for Eukaryotic Protein Synthesis", *Antisense Research and Development*, 3:171–179 (1993).

*Primary Examiner*—George C. Elliot
*Assistant Examiner*—Thomas G. Larson
*Attorney, Agent, or Firm*—Barry Dale Cash

[57] ABSTRACT

The inhibition of proteins synthesis by an antisense RNA-tRNA complex which is capable of inhibiting translation is described. Under certain conditions, growth of organisms is inhibited by inhibition of non-specific translation by an antisense RNA construct to a tRNA target. In vitro, cell-free inhibition of viral protein translation is described. Transformed microorganisms are disclosed. The invention has applicability in the control of cell growth, such as viruses, bacteria, infected cells, or tumor cells. The invention is useful in animal and plant fields.

36 Claims, 18 Drawing Sheets

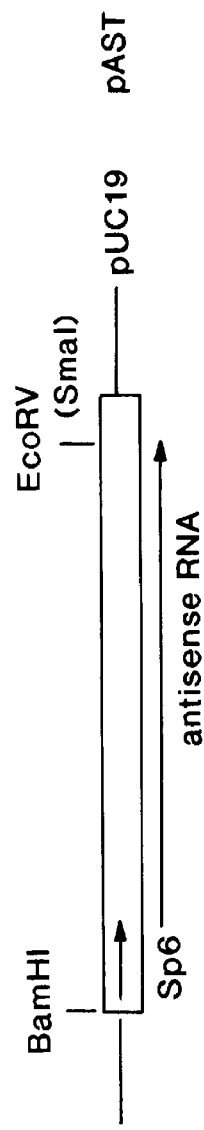

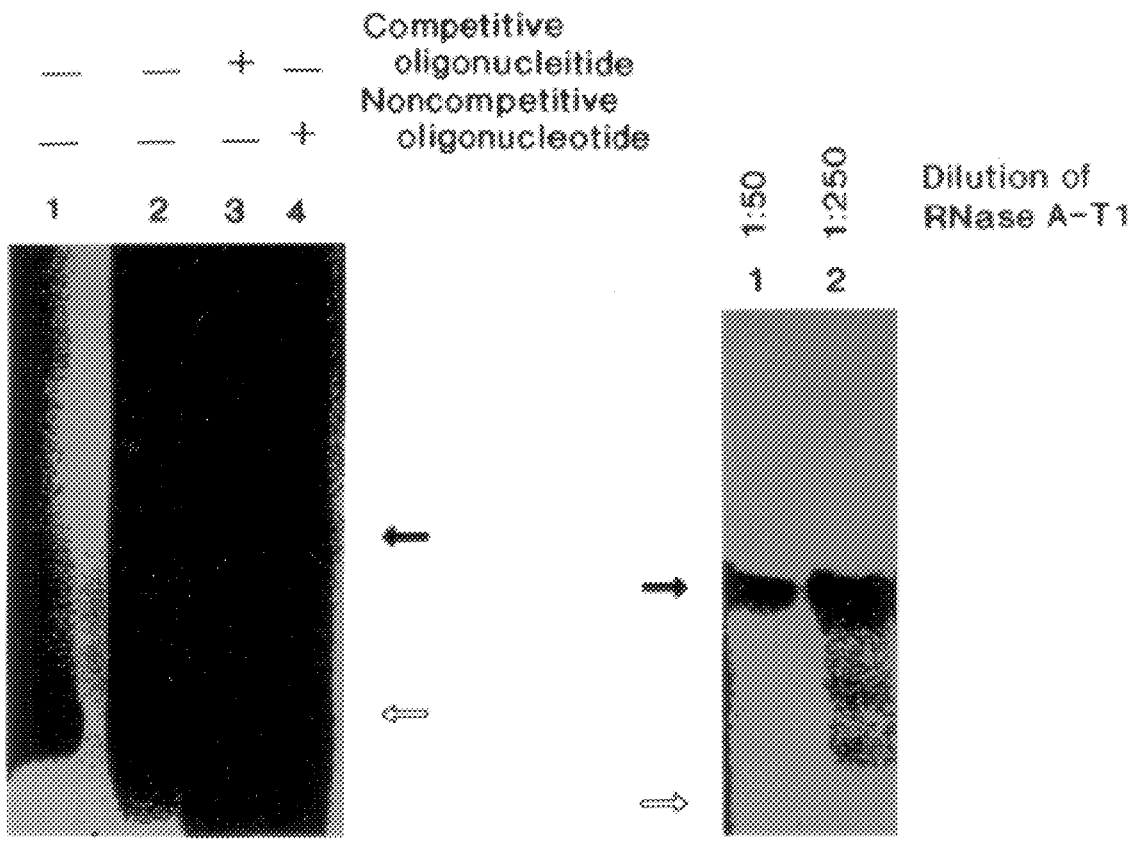
FIG. 13A
FIG. 13B
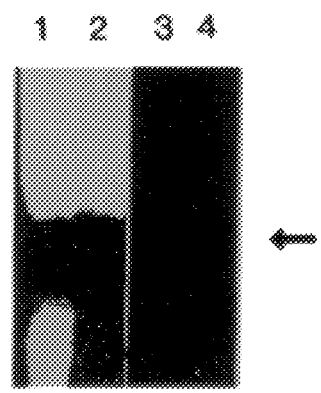
FIG. 13C

CONTROL OF THE SYNTHESIS OF PROTEINS BY ANITISENSE RNA-TRNA COMPLEX

RELATED CASES

This application is a continuing in part application of pending U.S. patent application Ser. No. 07/869,766, filed Apr. 16, 1992, now abandoned.

BRIEF DESCRIPTION OF THE INVENTION

The invention relates broadly to inhibiting translation and thus the synthesis of proteins. Under specified conditions, protein synthesis can be blocked in prokaryotes and in eukaryotes, hence inhibiting cell growth.

Regulation of cell growth by artificially constructed antisense RNA against tRNAs has never been reported. Antisense RNA against tRNAs thus may be used to non-specifically inhibit the expression of various cellular genes, providing a very effective method of blocking cell growth in organisms.

Antisense RNA against tRNAs may be applied toward the inhibition of viral infections and carrier cells. Specific promoters can be selected which are related to specific viruses or tumor cells to transcribe a gene for antisense tRNA, so that the inhibition of cell growth can be selective, only in virus-infected cells or specific tumor cells.

Antisense RNAs against tRNAs provide a method and molecules to control gene expression broadly and non-specifically and hence the potential of developing highly effective therapies for diseases known to result from excessive production of specific gene products or from the production of undesirable gene products.

The invention is applicable to inhibit translation in humans, animals and plants. It is contemplated that the synthetic construct harboring the antisense gene be incorporated into a cell whose translation is to be inhibited, such as a cancer or virus cell, thus inhibiting its growth without influencing healthy or normal cells adversely.

This growth inhibition has been accomplished in accordance with the invention by antisense RNAs construct targeted against tRNAs with a typical prokaryote, $E.$ $coli$. In vitro, the translation of Bromo Mosaic Virus (BMV) mRNA in a wheat germ extract was also blocked.

Antisense RNAs were used against a portion of original $tRNA_{AGA/G}$, formyl methionyl $tRNA_{AUG}$ or phenylalanyl $tRNA_{UUC}$. Using appropriate vectors, antisense RNAs against these tRNAs were expressed in $E.$ $coli$. It was found that in all cases, cell growth was severely inhibited upon induction of the antisense RNAs. As described in greater detail herein, the results suggest that protein synthesis is specifically blocked by the antisense tRNA. The invention also relates to a cell free system using tRNAs.

The invention which is applicable to all tRNAs. A tRNA is selected and a DNA oligonucleotide sequence is synthesized which is complementary to a sequence of the target tRNA. The antisense RNA fragment is cloned into an appropriate replicable vector which includes necessary regulatory elements so that the RNA transcript has an antisense configuration. A selected organism is transformed or transfected with the gene coding for the RNA capable of annealing to the target tRNA, thereby inhibiting translation and thus the proliferation of the organism.

BRIEF DESCRIPTION OF THE FIGURES

FIG. 3A shows a growth curve at 30° C. and then at either 30° C. or at 42° C. FIG. 3B shows a growth curve of the culture at 30° C. following a shift to 42° C. FIG. 3C shows a growth curve of a culture grown at 42° C. following a shift back to 30° C.

FIG. 4A shows relative cell growth at 30° C. and at 42° C. FIG. 4B shows relative $^{35}S$-methionine incorporation at 30° C. and at 42° C. of the cells of which the growth is shown in FIG. 4A. FIG. 4C shows relative cell growth at 30° C. and at 42° C. FIG. 4D shows relative [$^3H$] thymidine incorporation at 30° C. and at 42° C. of the cells of which the growth is shown in FIG. 4C.

FIG. 5A shows the growth curve of cells harboring the pGEM1 vector. FIG. 5B shows cells transformed with pGEM1-astRNA-Arg(AGA/G) for anti-$tRNA_{AGA/G}^{Arg}$. FIG. 5C shows the growth curve of cells transformed with pGEM1-astRNA-Phe(UUU/C) for anti-$tRNA_{UUU/C}^{Phe}$. FIG. 5D shows the growth curve for cells transformed with pGEM1-antRNA-Met(AUG) for anti-$tRNA_{AUG}^{fMe}$.

FIG. 6A shows tRNAs detected by Northern blot hybridization with use of a $^{32}P$-labeled oligonucleotide complementary to $tRNA_{AGA/G}^{Arg}$. FIG. 6B shows tRNAs detected by Northern blot hybridization with use of a $^{32}P$-labeled oligonucleotide complementary to $tRNA_{UUU/C}^{Phe}$.

FIG. 8A shows the growth curves for $E.$ $coli$ harboring pGEM1-astRNA-Arg(AGA/G). FIG. 8B shows the growth curves for cells harboring both pGEM1-astRNA-Arg(AGA/G) and pGEM2-anti-astRNA-Arg(AGA/G). FIG. 8C shows the growth curves for cells harboring pGEM2-anti-astRNA-Arg(AGA/G).

FIGS. 9A and 9B (Seq ID Nos. 4 and 5, respectively A, FIG. 9B, and FIG. 9C show the structure of antisense $tRNA^{met}$ and FIG. 9C shows recombinant plasmids. FIG. 9A shows the structure of antisense $tRNA^{met}$ and recombinant plasmids. FIG. 9B shows the synthesized DNA fragment to clone the antisense tRNA into plasmid DNA. FIG. 9C shows the structure of recombinant plasmids pAST and pGES used for in vitro transcription of antisense and sense RNA.

FIG. 11A shows the inhibition of BMV mRNA translation in vitro by antisense $tRNA^{met}$. FIG. 11B shows the analysis of proteins synthesized in wheat germ extract in the presence of control, antisense and sense RNA.

FIG. 13A shows the detection of antisense RNA-tRNA$^{met}$ complex in wheat germ extract. FIG. 13B shows the resistance of antisense NA-tRNA$^{met}$ complex to the RNAaseA-T1 mixture and FIG. 13C shows the detection of antisense RNA-tRNA$^{met}$ complex in wheat germ extract.

DETAILED EMBODIMENTS OF THE INVENTION

Antisense RNAs have been extensively used to block specific gene expression in both prokaryotes and eukaryotes. See Reference 1, for a review. For example, in prokaryotes the production of the *E. coli* major outer membranae lipoprotein was very effectively blocked by inducing a 112-base antisense RNA complimentary to the ribosome-binding region of the lipoprotein mRNA. Similarly, *E. coli* cells producing antisense RNAs against mRNAs of bacteriophage SP became immune against the infection with this phage. In the eukaryotes, there are also numerous reports inhibit specific gene expression from oncogenies to viral genes.

For another recent publication on developments in Antisense, see "Antisense, Research and Development", Vol. 1, No. 2, (summer 1991), Mary Ann Liebert, Inc. Publishers.

For artificial antisense RNA expression, part of a target gene is transcribed in the opposite orientation so that the RNA from the target gene can anneal and form a double-stranded RNA with the antisense RNA to inhibit the translation of the mRNA.

The invention provides a global, universal, non-specific control, inhibition or blockage of translation so as to control, inhibit or block protein synthesis. When in accordance with the invention the method is carried out in vivo, the growth of the organism is correspondingly controlled, inhibited or blocked.

Any of the known tRNAs can be selected to anneal with the antisense RNA. The selection of the tRNAs will be determined by one skilled in the art by the organism, the growth of which is sought to be inhibited. The synthesis of every protein of the organism, e.g., virus, (e.g. HIV) tumor cell, etc., which is dependent on translation from the tRNA selected will thus be inhibited.

In contrast to mRNAs, since tRNAs are much more abundant and stable in cells, they are considered less suitable than mRNAs for antisense targets. In accordance with the invention, it was found, however, that antisense RNA complementary to a portion or to all of a selected tRNA can effectively block the translation of mRNA. In contrast to the prior art classical antisense strategy, the invention provides not an inhibition of the translation of a specific mRNA encoding a specific protein which may be vital to the growth of an organism but a general, non-specific inhibition of translation of a particular cell. In one embodiment of the invention, the growth of a microorganism like that of *E. coli* was suppressed. In a second embodiment, the translation of a BMV mRNA in a wheat germ cell-free extract was blocked.

In accordance with one embodiment of the invention, it was found that antisense RNA complementary to a selected tRNA, particularly to a 5'-end sequence of certain tRNAs, specifically, arginyl tRNA$_{AGA/G}$, formyl methionyl tRNA$_{AUG}$, or phenylalanyl tRNA$_{UUC}$ effectively blocked cell growth of *E. coli*.

Figure 1A:
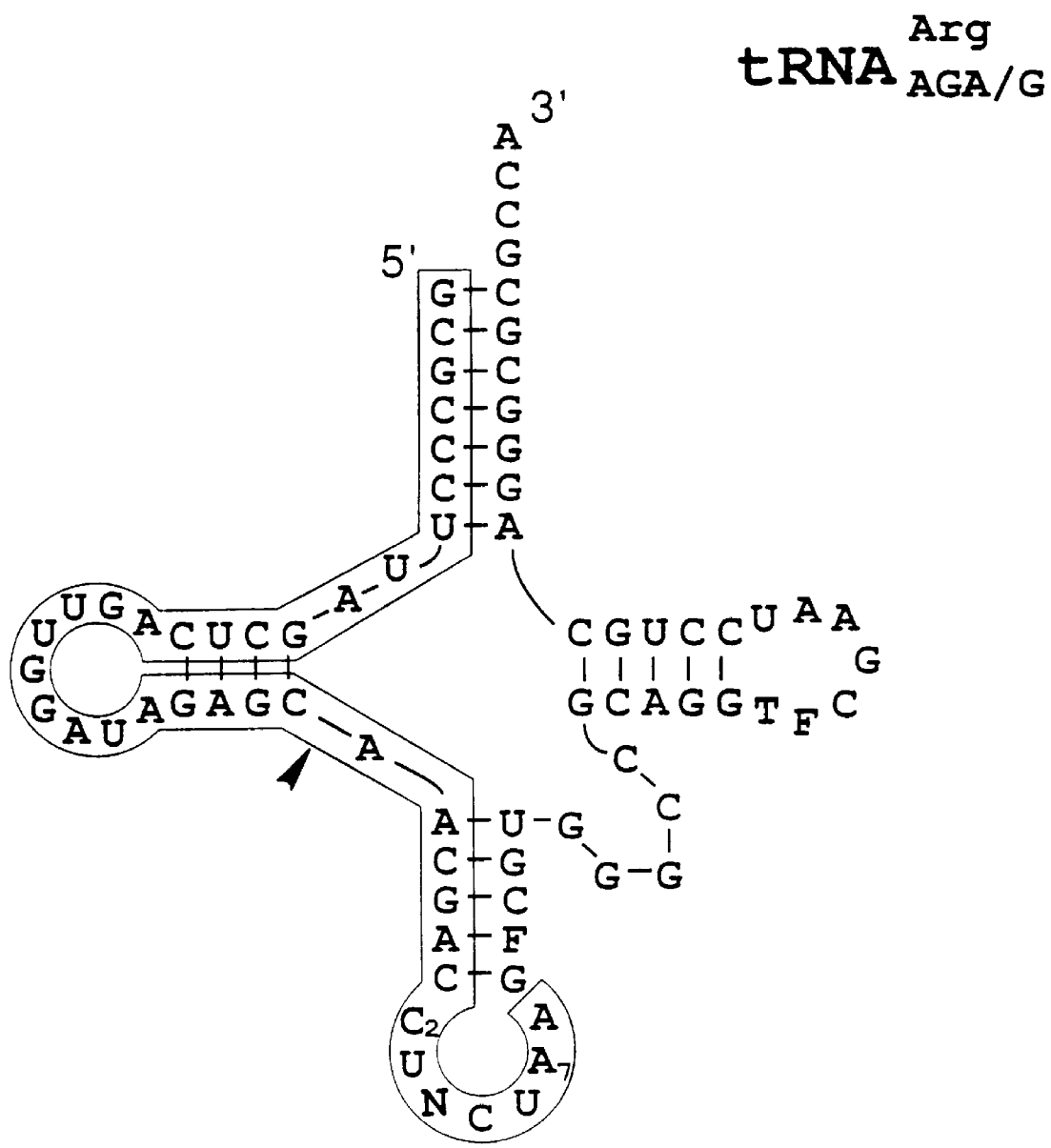
FIG. 1A, FIG. 1B, and FIG. 1C show the structure of the target tRNAs, respect for antisense tRNAs, $tRNA_{AGA/G}^{Arg}$ (Seq ID No. 1), $tRNA_{UUU/C}^{Phe}$(Seq ID No. 3), and $tRNA_{AUG}^{fMe}$, respectively (Seq ID No. 2).

In the work in connection with the invention, tRNA$^{Arg}$AGA/G, the least abundant tRNA in *E. coli* was selected as the target. An earlier attempt to express an antisense RNA against the entire tRNA$^{Arg}$AGA/G was not successful. In accordance with the invention, an antisense RNA gene against the 5'-end half of the tRNA as shown in FIG. 1A was constructed. The antisense RNA thus produced, is complementary to the tRNA sequence from the 5'-end G residue to the 39th A residue just encompassing the anticodon loop. This region was synthesized and inserted into the EcoRI-HindIII sites of pV2M$^6$ (FIG. 2A) so that the antisense RNA gene is under the control of the λ P$_r$ promoter. Because of the nature of the construct, the transcript has extra 5 bases (AATTC) and 55 bases at its 5' and 3' ends, respectively.

Figure 3A:
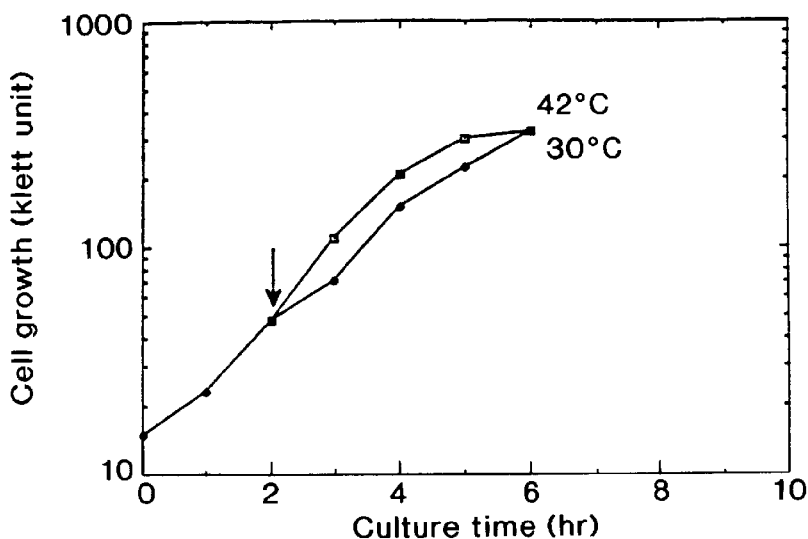
FIG. 3A, FIG. 3B, and FIG. 3C show the growth curves at low and high temperatures of $E.$ $coli$ transformed with pV2M and with pV2M-astRNA-Arg(AGA/G).
Figure 3B:
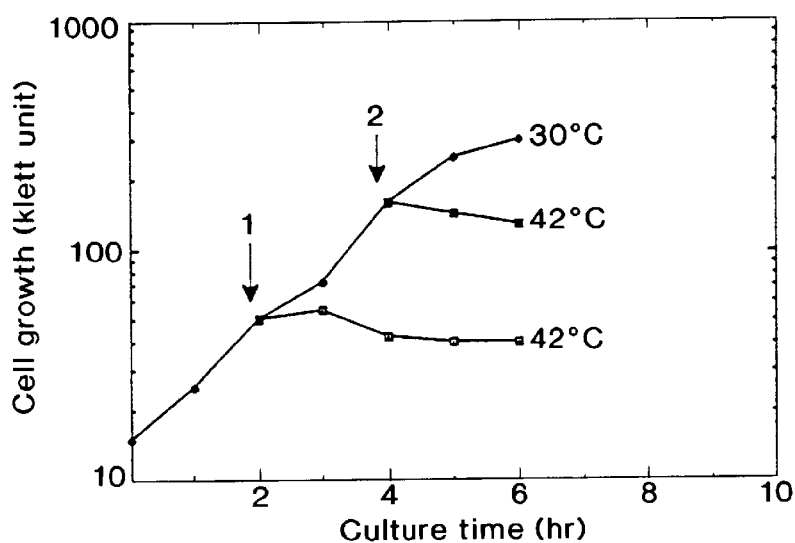

The P$_r$ promoter is repressed by the Cl repressor produced by the same vector. The Cl repressor is temperature-sensitive so that at 42° C. the cloned gene expression is induced. As shown in FIG. 3B, upon temperature shift from 30° C. to 42° C., the growth of *E. coli* cells transformed with pV2M-astRNA-Arg(AGA/G) abruptly stopped. The growth inhibition occurred either in mid log (arrow 1) or late log (arrow 2) phase. The cells carrying only the vector plasmid pV2M, grew normally upon the temperature shift (FIG. 3A).

Figure 3C:
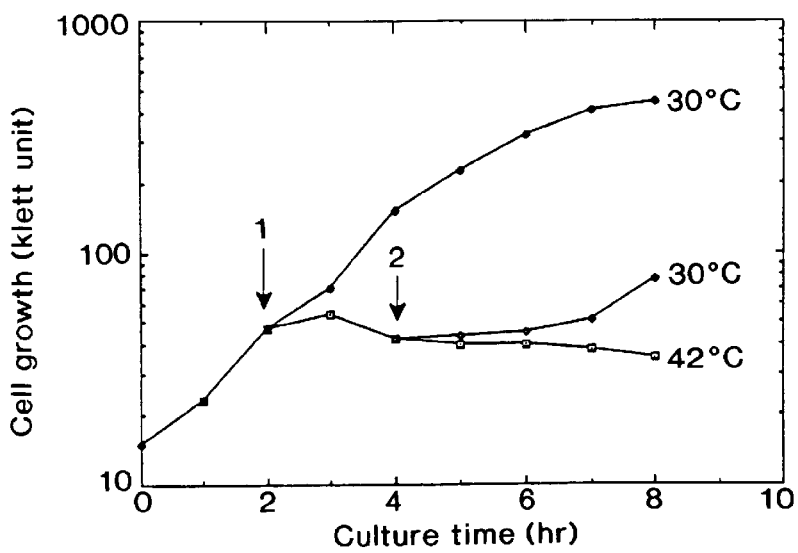

The cell growth inhibition was reversible under the time frame of the experiment as shown in FIG. 3C. When the growth temperature was shifted back to 30° C. after 2 hr incubation at 42° C., cell growth was resumed to the normal rate after an approximately 2.5 hr lag period. Cell growth eventually reached the same stationary level as the control culture (not shown). This result indicated that the cell growth inhibition is not due to irreversible damage in a cellular function(s) and that the cell growth inhibitor induced at 42° C. can be eliminated when the culture temperature is shifted back to 30° C.

Figure 4A:
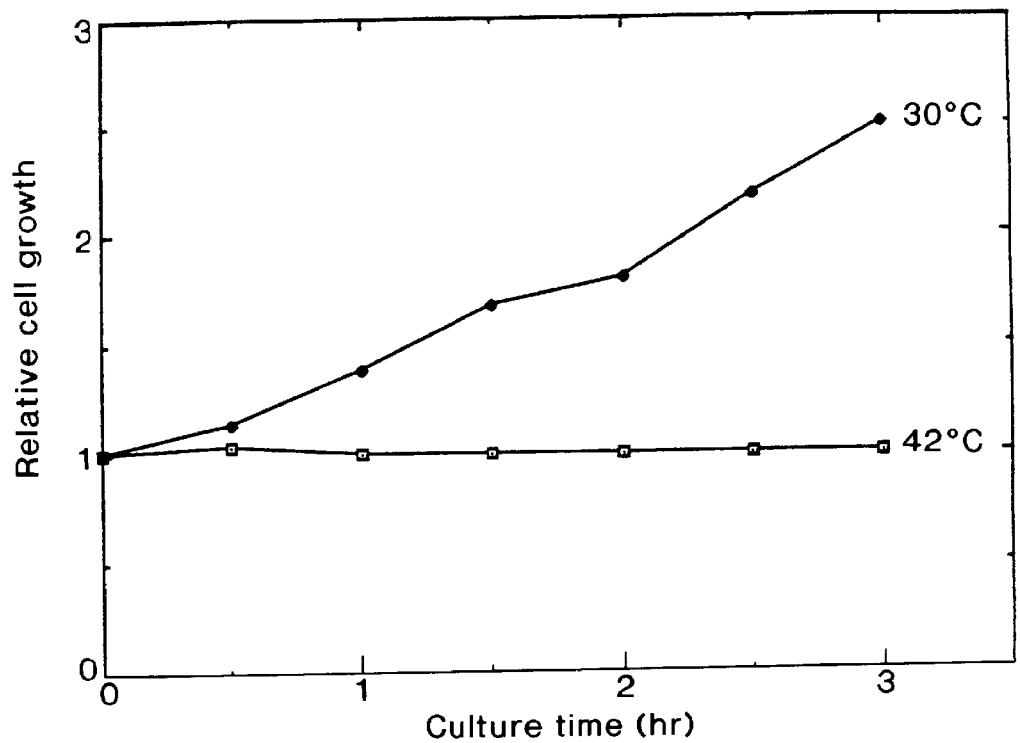
FIG. 4A, FIG. 4B, FIG. 4C, and FIG. 4D show the incorporation of $^{35}S$-methionine and $^3H$-thymidine after temperature shift.
Figure 4B:
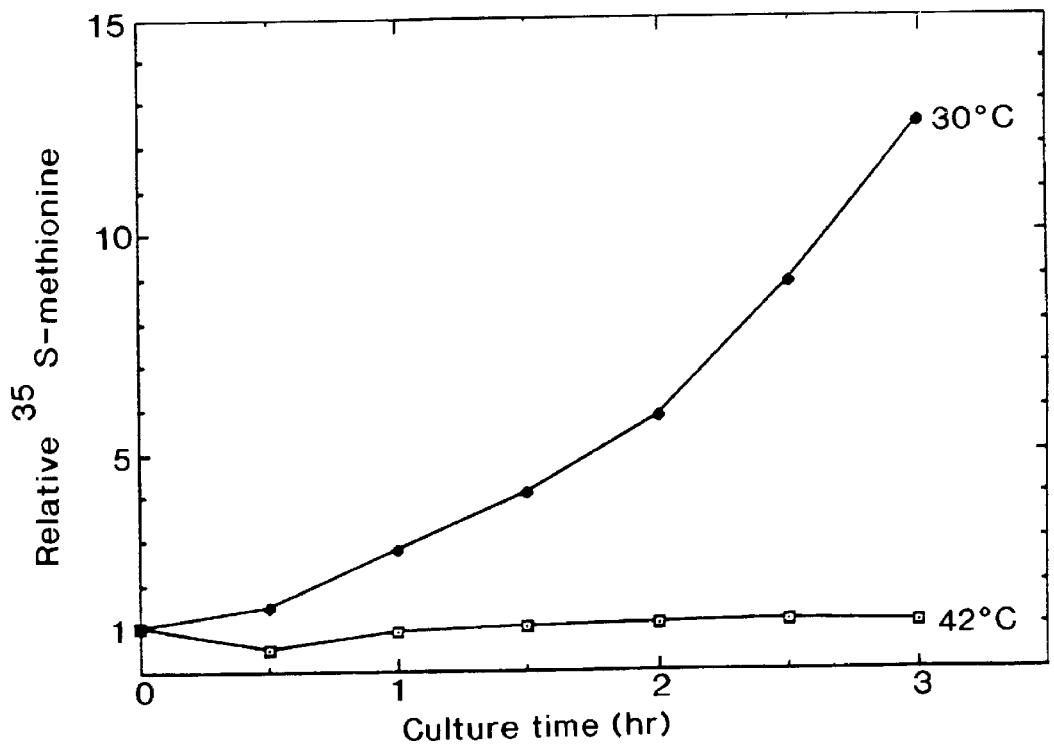
Figure 4C:
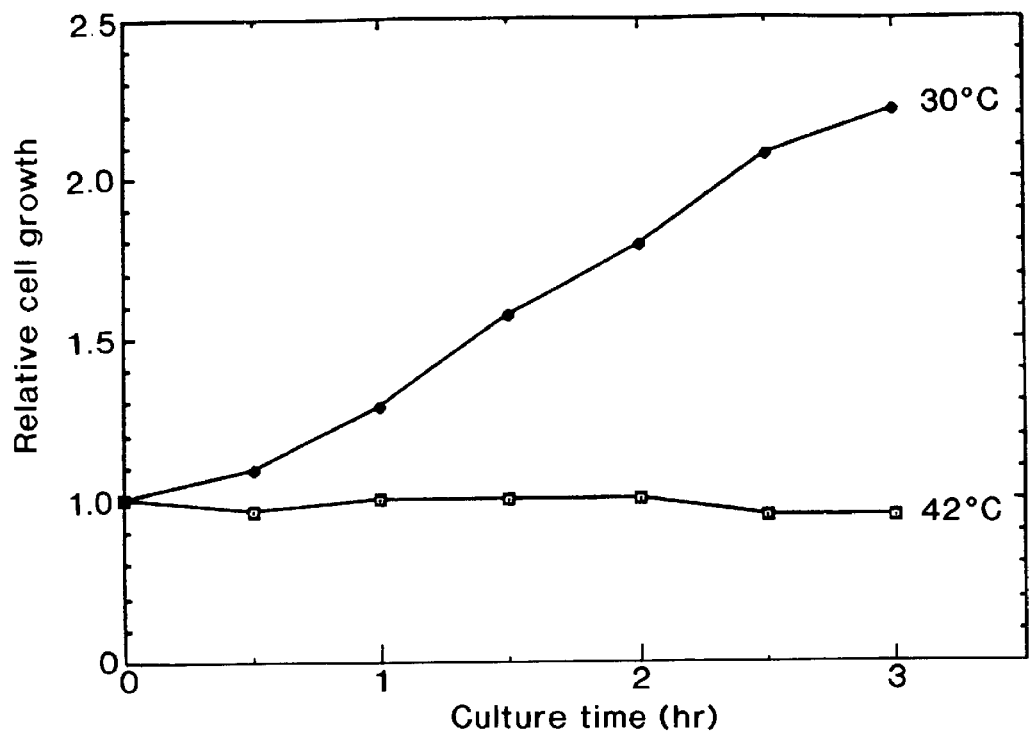
Figure 4D:
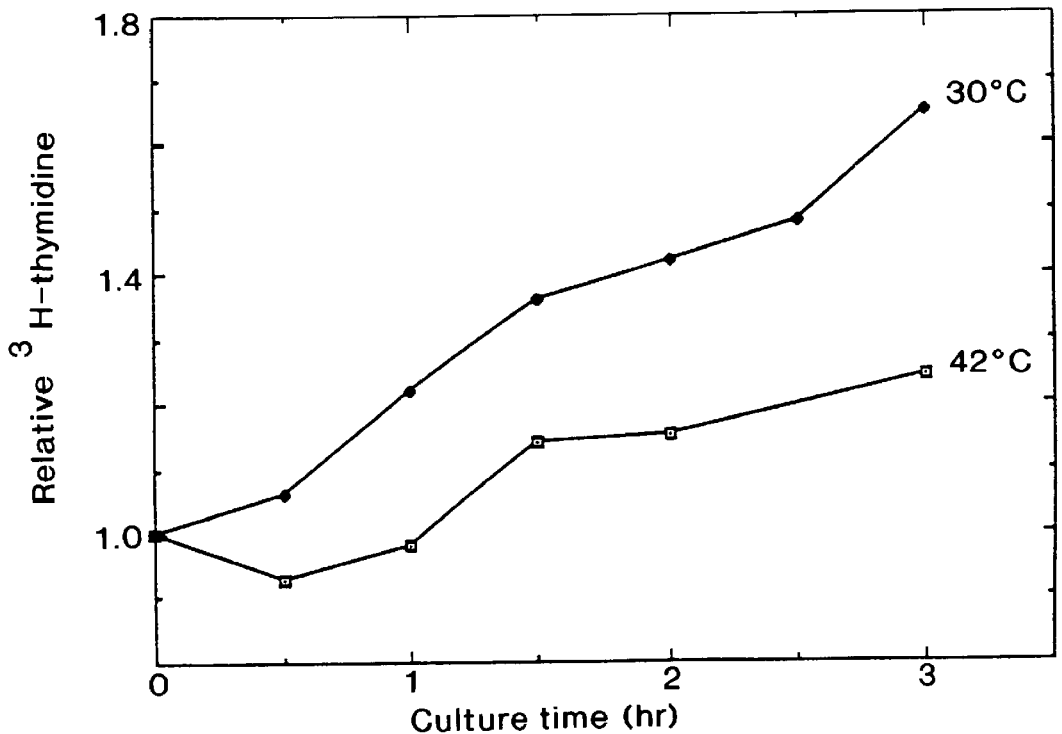

Protein and DNA synthesis during the cell growth inhibition was then studied. Cells harboring pV2M-astRNA-Arg (AGA/G) were grown at 30° C. in the presence of $^{35}$S-methionine for 2 hr. The culture was then split into two halves; one was kept at 30° C., while the other was shifted to a 42° C. incubator. As shown in FIG. 4A, cells grew normally at 30° C. but immediately stopped growing at 42° C. $^{35}$S-methionine incorporation continued at 30° C., while it stopped immediately after the temperature shift (FIG. 4B). In contrast, $^3$H-thymidine incorporation continued at 42° C. at a reduced rate as shown in FIG. 4D. There was a reproducible small reduction of the total-TCA precipitable radioactivity for the first one hr after induction. At present it is unknown why the $^3$H-thymidine incorporation did not increase for the first 1 hr and whether the $^3$H-thymidine incorporation after 1 hr was due to the chromosomal DNA replication or DNA repair. However, the viability of cells did not significantly drop during the 42° C. incubation; the viability after 6-hr incubation at 42° C. was 118% of the total viable cells at zero time. This result is consistent with the growth rate recovery upon shifting back the growth temperature from 42° C. to 30° C. as shown in FIG. 3C. It should be also noted that the growth inhibition was not due to general depletion of energy production in the cells since $^3$H-thymidine was able to be incorporated.

Figure 5A:
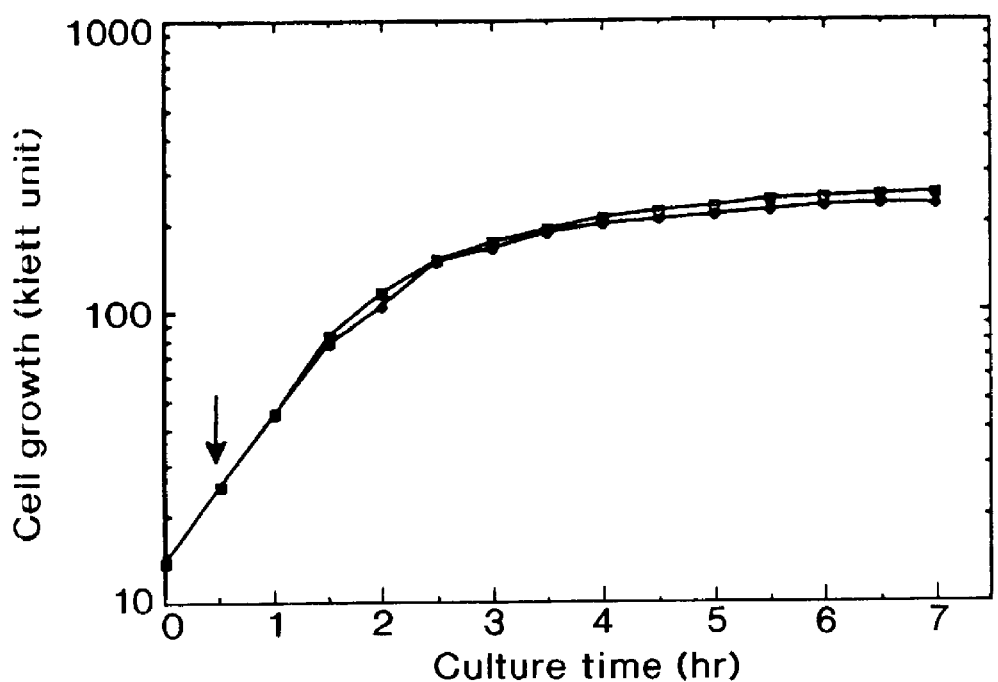
FIG. 5A, FIG. 5B, FIG. 5C, and FIG. 5D show the growth curves of $E.$ $coli$ BL21(DE3) transformed with pGEM1 and with pGEM1 harboring various antisense tRNA genes in the absence and the presence of IPTG.
Figure 5B:
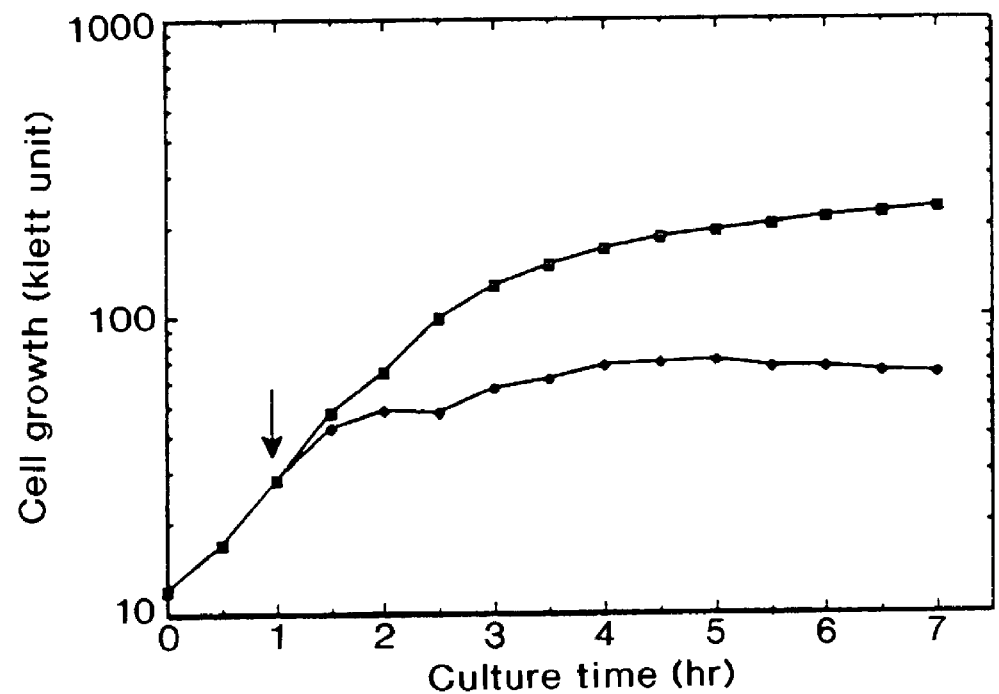

The effectiveness of anti-tRNA$_{AGA/G}^{Arg}$ described above may be due to the temperature-inducible expression vector used for the experiments. To test this possibility, a different promoter was used to express anti-tRNA$_{AGA/G}^{Arg}$. The vector pGEM1 containing both SP6 and T7 promoters was employed for this purpose (Studier and Moffatt, 1986). The same antisense tRNA fragment as used above was inserted between the EcoRI and PstI sites of the vector so that the transcript produced under the T7 promoter has an antisense configuration (FIG. 2B). The plasmid thus constructed was designated PGEM1-astRNA-Arg(AGA/G), and was transformed into the *E. coli* BL21(DE3) (Studier and Moffatt, 1986) which is capable of producing T7 RNA polymerase upon addition of a lac inducer, isopropyl-β-D-thiogalactopyranoside (IPTG). The addition of 1 mM IPTG had no effect on the growth of cells carrying only pGEM1 vector (FIG. 5A), while it caused severe growth inhibition of cells carrying pGEM1-astRNA-Arg(AGA/G) (FIG. 5B). In particular, approximately one hour after IPTG addition, cell growth was almost completely blocked. This result demonstrates that the growth inhibition observed above is independent from the promoter used for induction of the antisense tRNA production, and from the growth conditions under which the antisense tRNA production was induced.

Figure 1B:
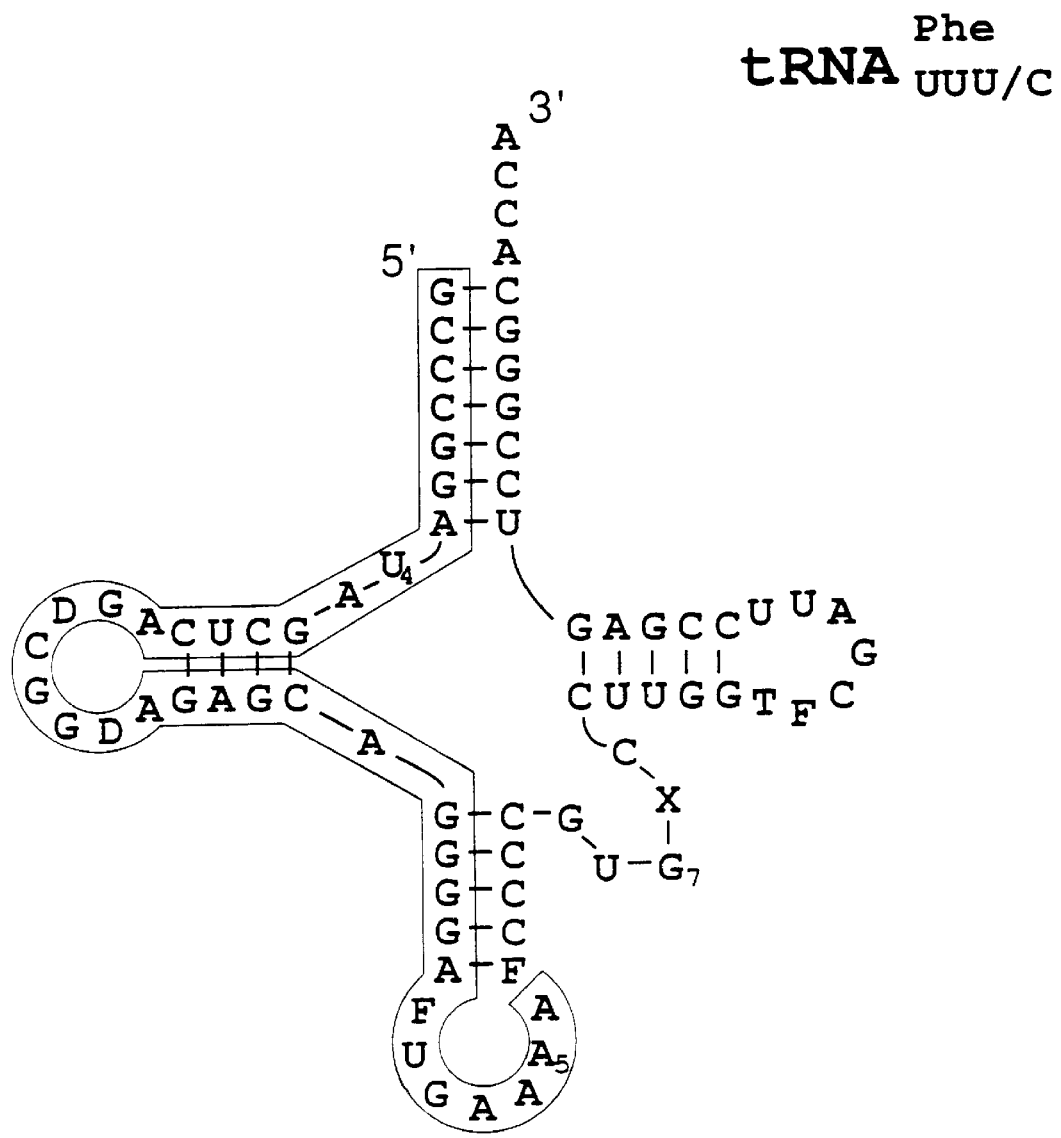
Figure 1C:
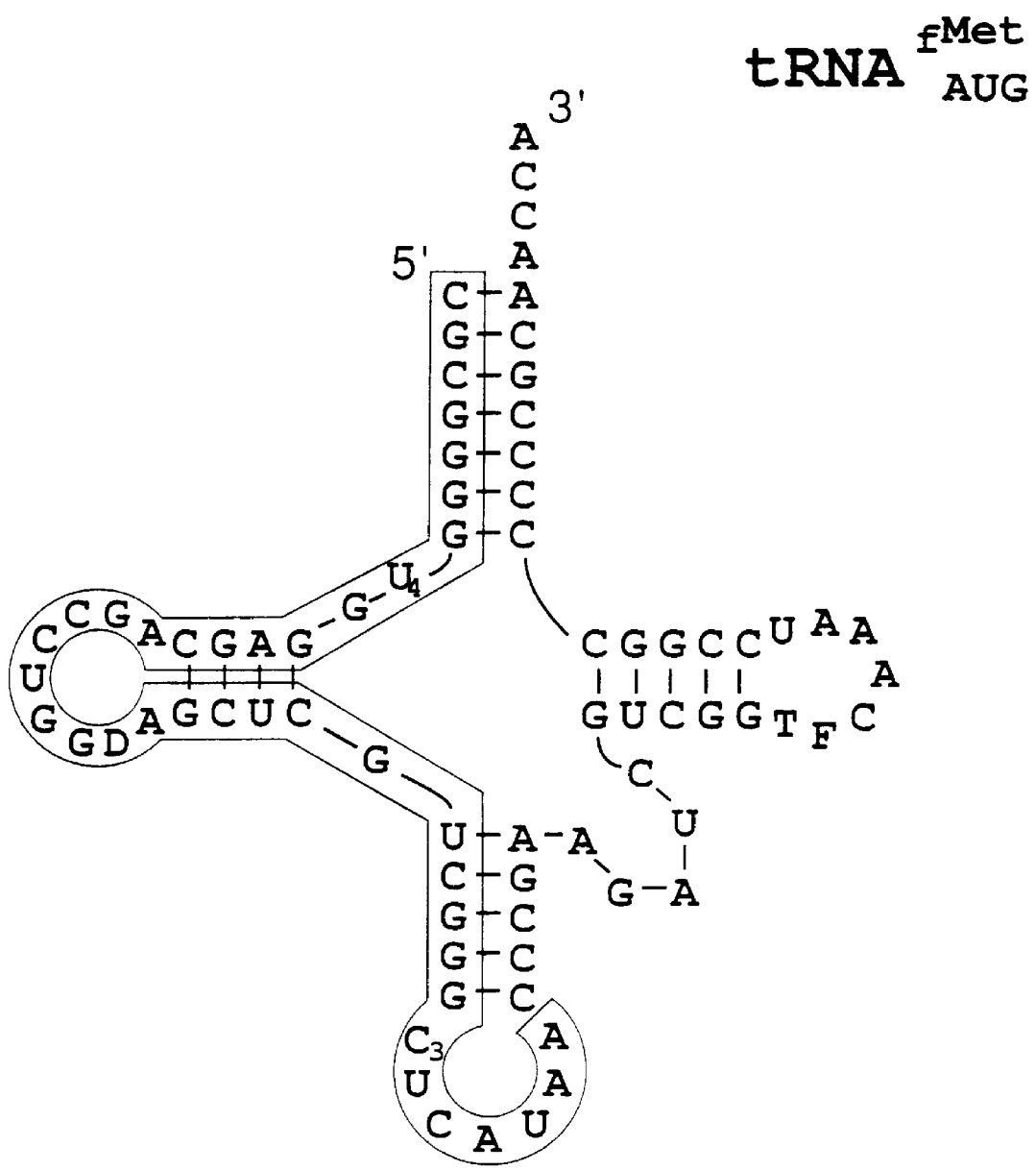
Figure 5C:
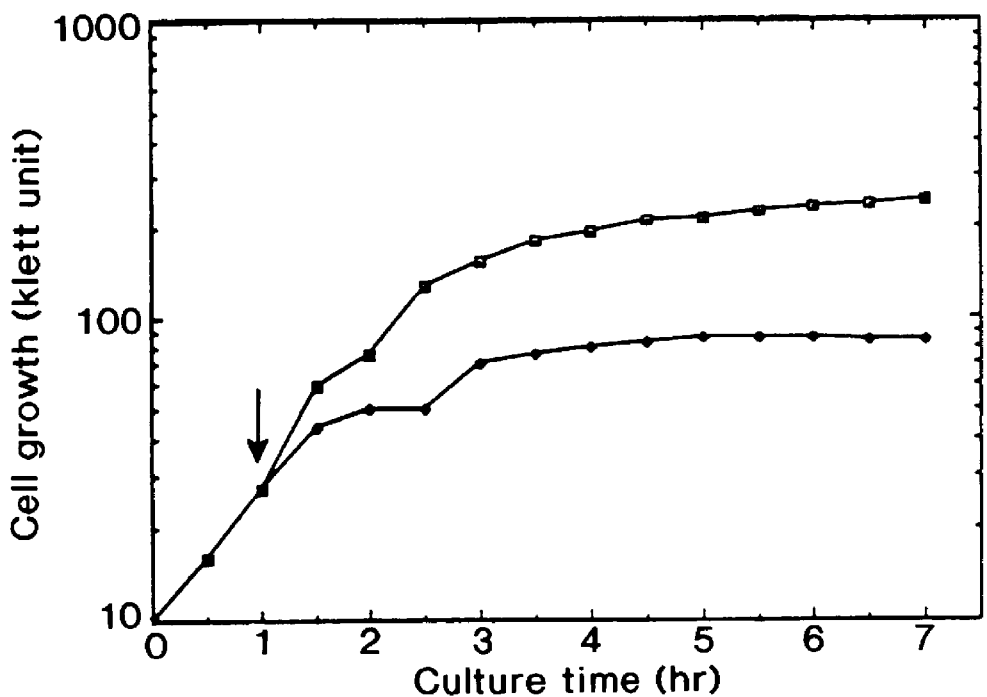
Figure 5D:
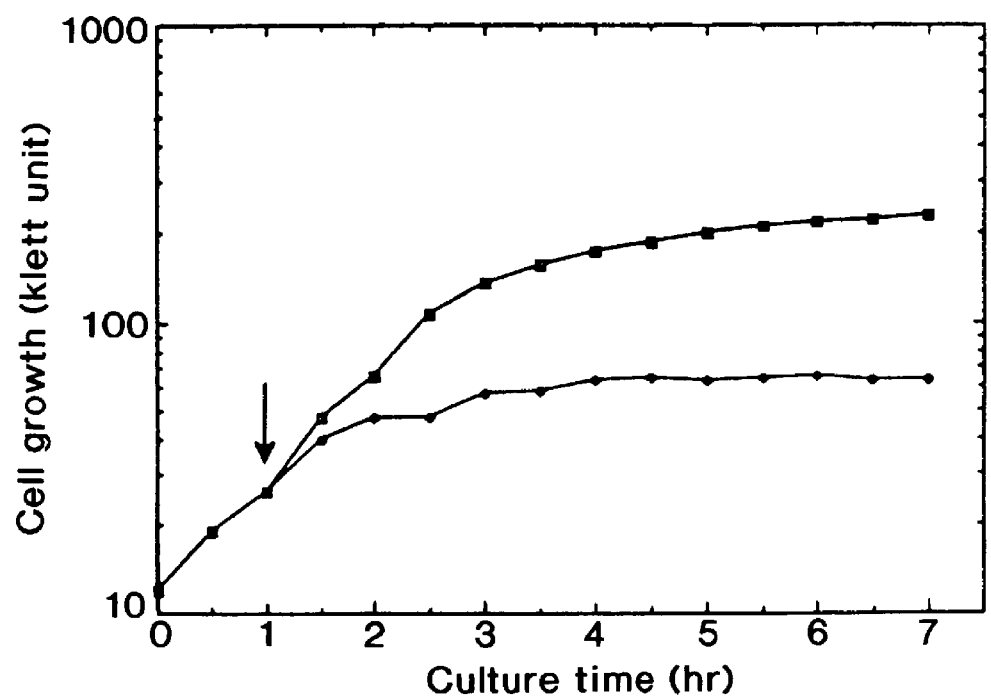

The effectiveness of anti-tRNA$_{AGA/G}^{Arg}$ described above may be due to the low abundance of tRNA$_{AGA/G}^{Arg}$ (Ikemura, 1981). We next examined the effects of antisense tRNAs against phenylalanine tRNA$_{UUU/C}$ and initiator methionine tRNA$_{AUG}$. Both amino acids are known to be coded individually by a single species of tRNA (Egan, et al., 1973; Barrell, et al., 1969). The tRNA structures and the target regions used for these antisense RNA are shown in FIGS. 1B and 1C for phenylalanine tRNA, and initiator methionine tRNA, respectively. The target regions were synthesized and inserted into the pGEM1 vector (FIG. 2B) in the identical manner as for anti-tRNA$_{AGA/G}^{Arg}$. Antisense tRNAs produced in the presence of IPTG are complementary to the tRNA sequences from the 3' end of the anticodon loop to the 5' end of tRNA as in the case of anti-tRNA$_{AGA/G}^{Arg}$. Induction of both anti-tRNA$_{UUU/C}^{Phe}$ (FIG. 5C) and anti-tRNA$_{AUG}^{fMet}$ (FIG. 5D) was found to be as effective as anti-tRNA$_{AGA/G}^{Arg}$ (FIG. 5B). This result indicates that tRNAs of high abundance can also be effective targets for antisense tRNAs in *E. coli*.

Figure 6A:
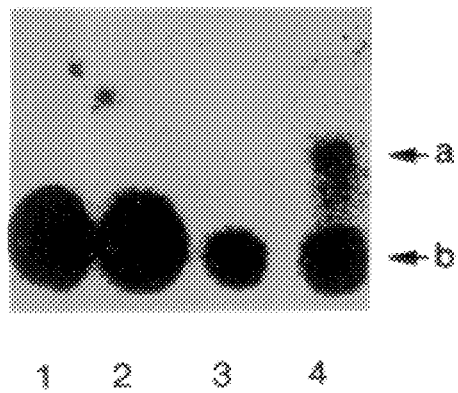
FIG. 6A and FIG. 6B show a Northern blot analysis of the effects of Anti-$tRNA_{AGA/G}^{Arg}$ on cellular tRNAs levels.

The effect of antisense tRNAs on the amounts of the target tRNAs in the cell was then examined. For this purpose, the amounts of arginine tRNA$_{AGA/G}^{Arg}$ were examined in the cells harboring pV2M-astRNA-Arg(AGA/G). The cells were grown at 30° C. and anti-tRNA$_{AGA}^{Arg}$ was induced for 1 hr at 42° C. Total tRNA fraction was then extracted and analyzed by formaldehyde-agarose gel electrophoresis. tRNA$_{AGA/G}^{Arg}$ was then detected by Northern blot hybridization with $^{32}$P-labeled antisense oligonucleotide against tRNA$_{AGA/G}^{Arg}$. As a control, total tRNA preparations were also analyzed from cells harboring the cloning vector, pV2M. As shown in FIG. 6A, there was no difference in the tRNA$_{AGA/G}^{Arg}$ (band b) quantity when comparing the cells grown at 30° C. (lane 1) and at 42° C. (lane 2).

However, the amount of the tRNA was substantially reduced in the cells harboring pV2M-astRNA-Arg(AGA/G) which were grown at 30° C. (lane 3). The induction of anti-tRNA$_{AGA/G}^{Arg}$ did not further reduce the amount of the tRNA (lane 4). However, there was induction of a new band (band a). The nature of band a is unknown at present.

Figure 6B:
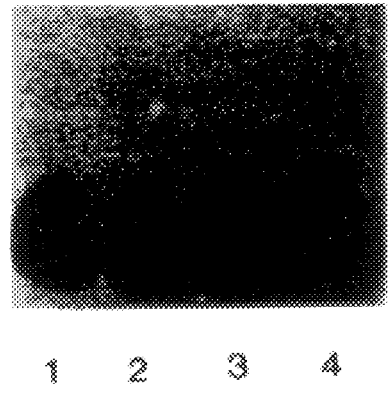

When the same RNA preparations used in FIG. 6A were tested by Northern blot hybridization with an antisense oligonucleotide probe against tRNA$_{UUU/C}^{Phe}$, no differences were observed among the same RNA preparation used above (lanes 1–4, FIG. 6B). Thus, pV2M-astRNA-Arg(AGA/G) clearly caused a specific effect on the amount of tRNA$_{AGA/G}^{Arg}$ in the cells even at 30° C. probably due to leakage of the expression of the anti-tRNA$_{AGA/G}^{Arg}$ at that temperature. The fact that no further reduction of the tRNA was observed upon heat induction of the antisense tRNA is somewhat puzzling. It is possible that the tRNA production was reduced at 30° C. to the level observed in lane 3, FIG. 6A (approximately 20% of the control level in lane 1) and that this amount of tRNA$_{AGA/G}^{Arg}$ was still enough to support the cell growth. Upon heat induction of the antisense tRNA, the function of the tRNA was probably hampered at the level of an arginyl-tRNA synthetase, and/or at the level of translation. These inhibitory effects might be caused by a sudden burst of the antisense tRNA production resulting in the formation of partial duplexes between the tRNA and the antisense tRNA, which then sequestered the functional tRNA away from protein synthesis. Such duplexes might be stable under the present conditions causing sudden cessation of cell growth (FIG. 3B) without further reduction of the amount of the tRNA in the cell.

Figure 7A:
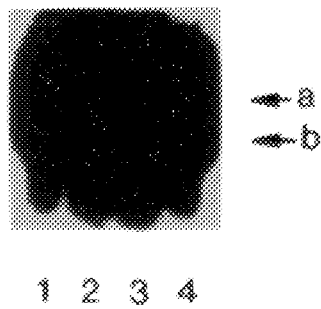
FIG. 7A and FIG. 7B show the effects of anti-$tRNA_{AGA/G}^{Arg}$ induced by IPTG on cellular tRNAs. $tRNA^{Phe}$ (FIG. 7A) and $tRNA^{Arg}$ (FIG. 7B) were detected by RNase protection analysis.
Figure 7B:
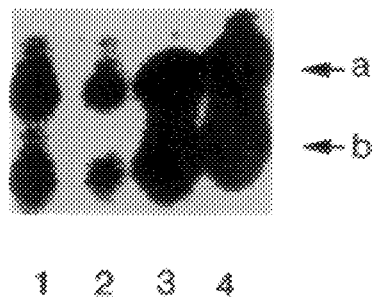

The amounts of tRNA$_{AGA/G}^{Arg}$ in the cells harboring pGEM1-ast-RNA-Arg(AGA/G) in the absence and the presence of IPTG were then studied. The tRNA was detected by ribonuclease protection assay as described in Experimental Procedures. The RNA preparation from the control cells in the absence (lane 3, FIG. 7B) and the presence (lane 4) of IPTG showed no difference in the amount of the tRNA, which showed two protected bands (a and b) under the condition used. The RNA preparation form the cells harboring the plasmid for antisense tRNA again showed a reduced amount of the tRNA even in the absence of IPTG (lane 1). In the presence of IPTG, however, it was further reduced to approximately 10% of the normal level (compare lane 2 with lane 4). In contrast, no change was observed for the amount of phenylalanine tRNA (lanes 1–4, FIG. 7A) in the same RNA preparations used for tRNA$_{AGA/G}^{Arg}$ (lanes 1–4, FIG. 7B, respectively). These results support the notion that an antisense tRNA reduces the amount of the target tRNA.

Anti-antisense tRNA Blocks the Inhibitory Effect of Anti-tRNA

As described above, if the direct targets of antisense tRNAs are tRNAs, the inhibitory effect of antisense tRNAs should be able to be blocked by RNAs complementary to antisense tRNAs, anti-antisense tRNAs. Anti-antisense tRNAs would form double-stranded cell growth. To test this, the same DNA fragment used for anti-tRNA$_{AGA/G}^{Arg}$ was inserted in the same orientation as tRNA in the pGEM2 plasmid so that the 5' end half of the tRNA$_{AGA/G}^{Arg}$ (base 1 to 39) or anti-anti-tRNA$_{AGA/G}^{Arg}$ could be produced in the presence of IPTG. The resulting plasmid was designated pGEM2-anti-astRNA-Arg(AGA/G) in which the gene for ampicillin resistance was replaced with the gene for kanamycin resistance. In cells harboring pGEM1-astRNA-Arg (AGA/G) growth stopped in the presence of IPTG (FIG. 8A) as previously shown in FIG. 5B. However, this inhibitory effect by the antisense tRNA disappeared when the cells were double transformed with pGEM1-astRNA-Arg(AGA/G) and pGEM2-anti-astRNA-Arg (AGA/G). The growth of the double-transformed cells grown in the presence of both ampicillin and kanamycin was not inhibited by the addition of IPTG (FIG. 8B).

Interestingly, the growth of cells harboring only pGEM2-anti-astRNA-Arg(AGA/G) was also inhibited in the presence of IPTG (FIG. 8C), indicating that the 5'-end half of the tRNA molecule also functions as a growth inhibitor. This is not surprising in veiw of the fact that either 5' or 3' half of a tRNA molecule is indeed partially complementary to the other half of the molecule (see FIG. 1). Thus, the 5' half of tRNA$_{AGA/G}^{Arg}$ used for the present experiment was likely to function as a kind of antisense tRNA as well by interacting with the 3' region of the tRNA in the absence of anti-tRN$_{AGA/G}^{Arg}$.

As described herein, it was demonstrated that antisense tRNAs function as effective cell-growth inhibitors. This result may be somewhat surprising in view of the fact that the target tRNAs are abundant in the cell and highly stable because of their secondary structures. However, the present results suggest that tRNAs may form a duplex or be unfolded if appropriate complimentary RNAs are provided. Indeed in the cell, the anticodon loop is able to form a duplex with a specific codon on an mRNA. In addition, some tRNAs have been shown to be used as primers for the initiation of retroviral cDNA synthesis by following a duplex with the viral RNA (See Varmus and Swanstrom, 1985 for review).

The antisense tRNA molecules used were complementary to the 5'-end halves of tRNAs having little secondary structure (see FIG. 1). Except for a short stem structure at the center corresponding to the dehydrouridine loop, they have single-stranded structures at both 5' and 3' ends. These single-stranded structures are probably important for unfolding of the target tRNAs, since the RNA molecule complimentary to the entire tRNA had little effect on cell growth. It is important to note that a shorter antisense tRNA was also a very effective growth inhibitor.

An antisense tRNA against the 5'-end 26-base sequence (base 1 to 26 as shown by an arrow in FIG. 1A) was able to block cell growth as effectively as the antisense tRNA against the 5'-end half (base 1 to 39).

Antisense tRNAs used are likely to interact directly wit their target tRNAs. The formation of double-stranded duplexes between tRNAs and antisense tRNAs causes sequestering functional tRNAs from the protein synthetic machinery. This notion can be supported by the fact that $^{35}$S-methionine incorporation was inhibited, while $^3$H-thymidine incorporation was not. In addition, a complementary RNA against an antisense tRNA (anti-antisense tRNA) was able to resume cell growth inhibited by the antisense tRNA (FIG. 8).

The present results raise some interesting possibilities about the uses of antisense tRNAs. Antisense tRNAs could be utilized as a general cell-growth regulator not only in prokaryotes but also in eukaryotes. In a eukaryotic cell-free system for protein synthesis, we were able to block $^{35}$S-methionine incorporation by antisense RNA against initiator methionine tRNA (O. Mirochnitchenko and M. Inouye, manuscript in preparation).

The invention contemplates transforming other organisms, prokaryotes and eukaryotes (notably various yeasts, mammalian or plant cells) with vectors harboring suitable selected antisense RNA genes and thus inhibiting the cell growth of the organism. A selected tRNA common in such organism dictates the nature of the antisense RNA.

In a second embodiment of the invention, it was found that antisense RNA complementary to the 5'-end half of the initiator methionine tRNA of wheat germ can effectively block the translation of BMV mRNA in a wheat germ cell-free system. It was also demonstrated that under the condition used in the cell-free system, the antisense tRNA formed a double-stranded hybrid with the target tRNA$^{met}$.

Figure 9A:
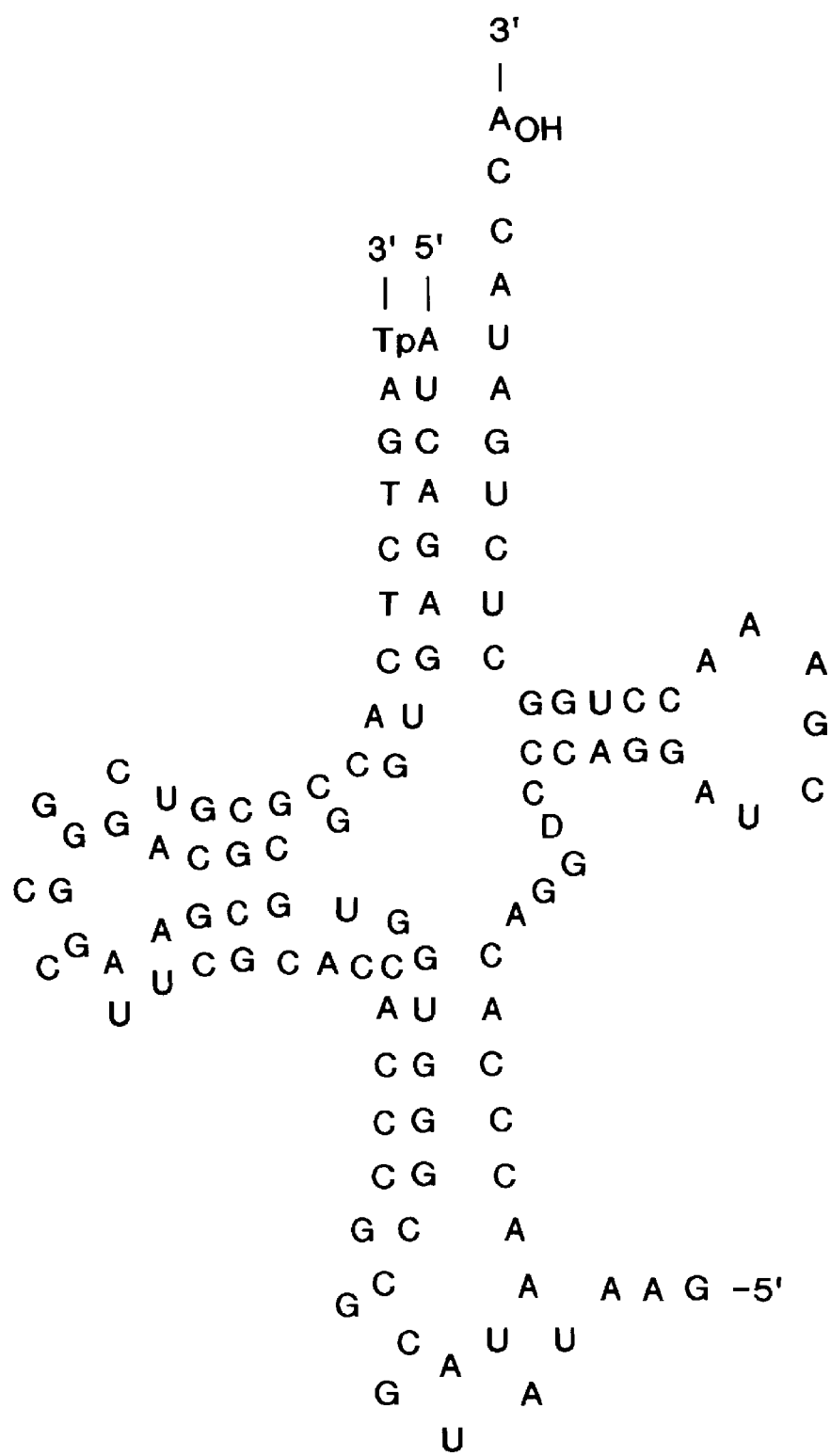

The antisense tRNA$^{met}$ was constructed as follows. The structure of antisense tRNA$^{met}$ which was used in this work is shown in FIG. 9A. It is complementary to the 5'-half of tRNA including anticodon. For preparation of antisense RNA, there was used an in vitro transcription system and a DNA fragment containing chemically synthesized oligonucleotides (FIG. 9B). An Sp6 promoter region and an EcoRV site were introduced in this fragment in order to obtain RNA with a minimum of additional nucleotides. For obtaining antisense RNA template, pAST was linearized by EcoRV and using Sp6 polymerase (FIG. 9C).

Sense RNA was synthesized by T7 polymerase from pGES cut by Hphl (FIG. 9C). The expected size of antisense RNA is 39 nucleotidase, and sense RNA, 70 nucleotides. As a template for synthesis of control RNA, pGEM2 was cut by several enzymes: SmaI, BamHl and EcoRl and RNA with length of 38, 45 and 56 nucleotides was obtained.

Figure 10:
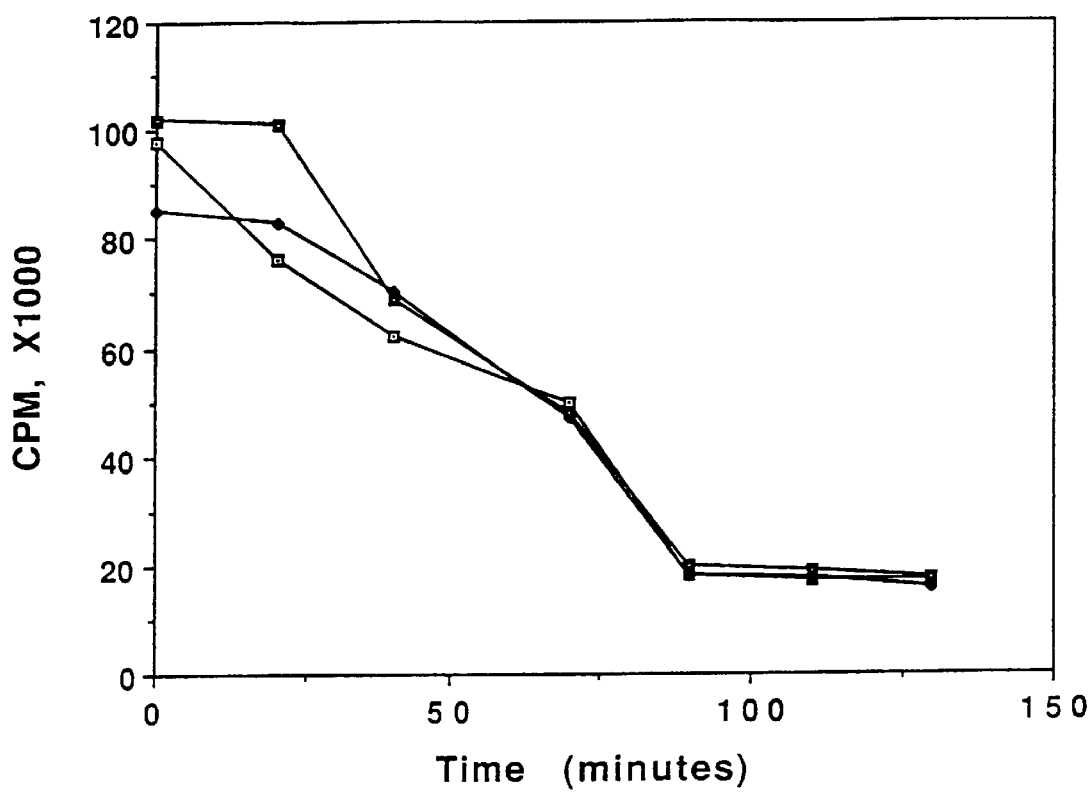
FIG. 10 shows the stability of antisense $tRNA^{met}$ in wheat germ extract.

Stability of antisense tRNA$^{met}$ in wheat germ extract. One of the most important parameters that influences the efficiency of antisense RNA inhibition is the speed of its degradation. To check how much added RNA survived at different incubation intervals in wheat germ extract, there was introduced into the reaction mixture a labeled antisense RNA and the quantity of acid precipitatable radioactivity was measured. As shown in FIG. 10, after the standard incubation time (one hour), near 60% of added labeled RNA was still present in reaction mixture. According to the results of polyacrylamide gel electrophoresis analysis, most of this activity belongs to the nondegradated RNA. Addition of cold antisense RNA up to the working concentration (8 $\mu$M) or ribonuclease inhibitor does not change the speed.

Effect of antisense tRNA$^{met}$ on translation of BMV mRNA in wheat germ extract. To investigate the action of antisense tRNA on the efficiency of in vitro translation, wheat germ extract was preincubated in the presence of different concentrations of antisense, sense or control RNA, then synthesis was initiated by addition of reaction mix, and at the end of the reaction, the incorporated radioactivity and protein pattern were checked by electrophoresis. As a mRNA, there was used BMV RNA.

It is known that the effect of different antisense agents can be improved by previous incubation with target RNA at higher temperature. This helps to anneal both types of nucleic acids. It was found that, even a short heating of wheat germ extract drastically reduced incorporation of radioactivity. Therefore, only preincubation at reaction temperature was used. Much clearer results were obtained in comparison with experiments without preincubation.

Another important parameter that has to be taken into consideration is the quantity of target RNA. To measure concentration of tRNA$^{met}$, there was used a RNase protection assay. According to the result of this assay, tRNA$^{met}$ was present in the extract of 0.2 $\mu$M. For many systems it was shown that for optimum efficient inhibition of RNA expression it is best to have 10 times molar prevalence of antisense RNA to target mRNA. In this work, there was used at least 2 $\mu$M of tRNA$^{met}$. The effect of different concentrations of sense, antisense and control RNA is shown in FIG. 11. At a 4 $\mu$M concentration of antisense RNA, mRNA synthesis was inhibited by 75%; at the same concentration control RNA revealed only slightly lower incorporation of Met in comparison to the basic level of in vitro translation. It was unexpected that sense RNA had a much greater effect than all the tested control RNAs (inhibition of 63% at concentration 4 $\mu$M). Since RNA action can be explained by its interaction with the second half of tRNA molecule via 14 complementary nucleotides. At concentrations more than 8 $\mu$M, there was obtained non-specific inhibition by control RNA. The pattern of proteins, synthesized in vitro under the addition of a different type of RNA reflects data obtained by measuring incorporated radioactivity (FIG. 11B). The effects of antisense and control RNA at different time points on translation activity of wheat germ extract are shown at FIG. 12.

Detection of complex between asRNA and tRNA$^{met}$. As described above, one of the most likely ways of action of antisense RNA is the forming of complex with target RNA. In order to try to detect the complex of antisense RNA and tRNA$^{met}$, there was introduced to the extract labeled antisense RNA, and after the reaction, a probe was loaded on the non-denaturing polyacrylamide gel (FIG. 13A). At the same time in some probes, there was added competitive (complementary to the target RNA) or non-competitive oligonucleotides. One can see at FIG. 13A appearance of a new band, which disappeared in the presence of competitive oligonucleotide. After pre-incubation, the quantity of complex slightly raised. At the end of the reaction, no detectable band corresponding to the complex was detected. Complex was resistant to the RNase A-T1 mixture of 37° C. (FIG. 13B).

Figure 14:
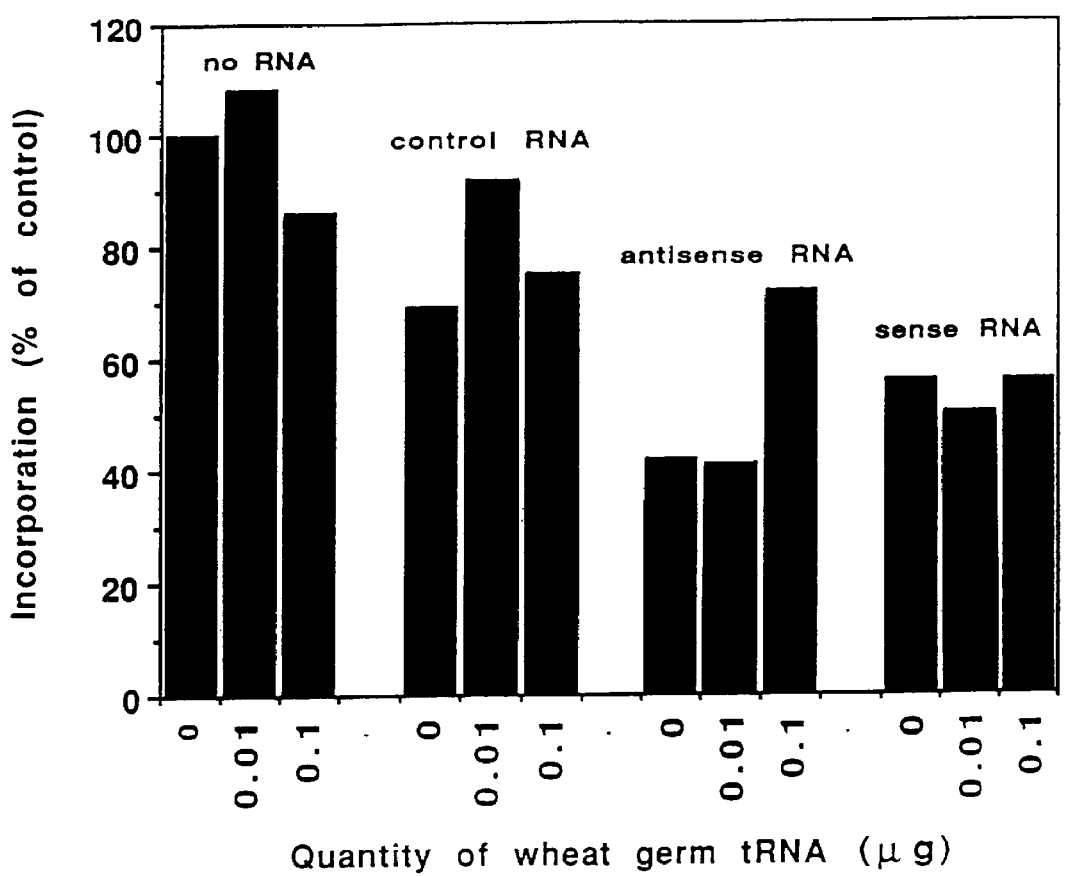
FIG. 14 shows the influence of additional tRNA on the inhibition of BMV mRNA translation in wheat germ extract by antisense RNA.

In order to obtain additional proof that this is a complex with tRNA$^{met}$, the same experiment was carried out only with non-labeled antisense RNA and after electrophoresis the gel was blotted to the nylon membrane and hybridized with labeled oligonucleotide complementary to the sequence of the loop at the 3'-end of tRNA$^{met}$ (FIG. 13C). As one can see from the results of this experiment, the only band detected is exactly at the same position as corresponding to the complex band. Antisense RNA (8 µM) was used for the assay. At this concentration, most of the tRNA molecules were in interaction with antisense RNA molecules. For effective and optimum inhibition, it is best to achieve a definite high enough antisense RNA concentration in the reaction mixture. This can be achieved, it is believed, by introduction of additional tRNA molecules. When the influence of additional tRNA on the basal level of in vitro translation was checked, it was found that at higher concentrations it decreased the efficiency of reactions, and at low concentrations even slightly activated the efficiency (FIG. 14). The same pattern was observed when there was added additional tRNA into the extract in the presence of 5 µM of control RNA. In the case of antisense RNA, a decrease (by 36%) of the inhibitory effect was observed after the addition of excess tRNA to the extract. When the quantity of tRNA was lower than necessary for binding to all antisense molecules, a considerable inhibitory effect became visible again. The influence of sense RNA on mRNA translation has intermediate character. At the concentration of sense RNA used, it was found that inhibition has at the same time, specific and non-specific effects.

As described above, in the antisense RNA-tRNA complex which is capable of inhibiting translation, the antisense RNA is complementary to less than the entire tRNA. It is not to be excluded however, that under certain conditions and with certain tRNAs, this condition need not apply. Further, it is contemplated that the antisense RNA be complementary to the 3' region or to the 5' region. And any region of tRNA can be used as the target for the antisense RNA. Further, although the embodiments exemplified in this application were complementary to the anticodon portion of the rRNA, it is not to be excluded that the antisense tRNA of the invention be complementary to portions other than, and not including, the anticodon portion.

DETAILED DESCRIPTION OF THE FIGURES

FIGS. 1A, B, and C shows the structure of tRNA$_{AGA/G}^{Arg}$, tRNA$_{UUU/C}^{Phe}$, and tRNA$_{AUG}^{fMe}$. The boxed regions were used as the target for antisense tRNA. In FIG. 1A, a smaller target region from the 5' end to base 26 was also used which is shown by an arrow. In addition to U, C, A and G, the following abbreviations are used for modified nucleotides; A$_5$, 2-methylthio-N6-isopentenyladenosine; A$_7$, N-((9-beta-D-ribofuranosylpurine-6-yl)carbamoyl)-threonine; C$_2$, 2-thiocytidine; C$_3$, 2'-O-methylcytidine; D, dihydrouridine; F, pseudouridine; G$_7$, 7-methylguanosine; N, a 5'-substituted 2-thiouridine derivative; T, 5'-methyluridine; U$_4$ 4-thiouridine; X, 3-(3-amino-3-carboxypropyl) uridine.

Figure 2A:
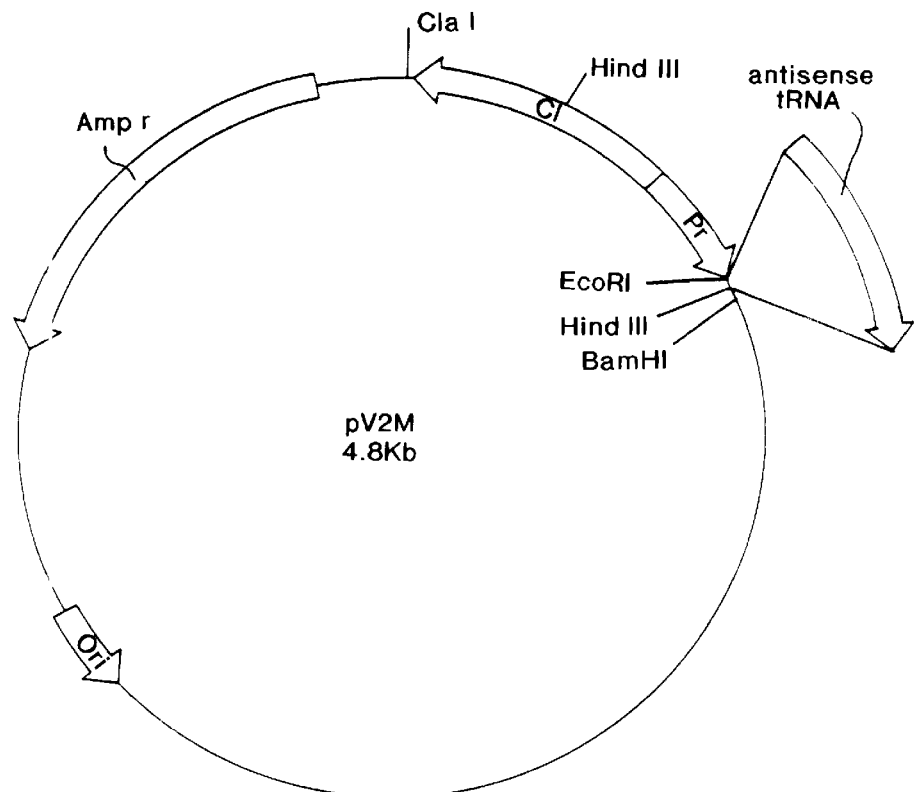
FIG. 2A and FIG. 2B show the structures of plasmid vectors, pV2M and pGEM1, respectively, for antisense tRNAs.
Figure 2B:
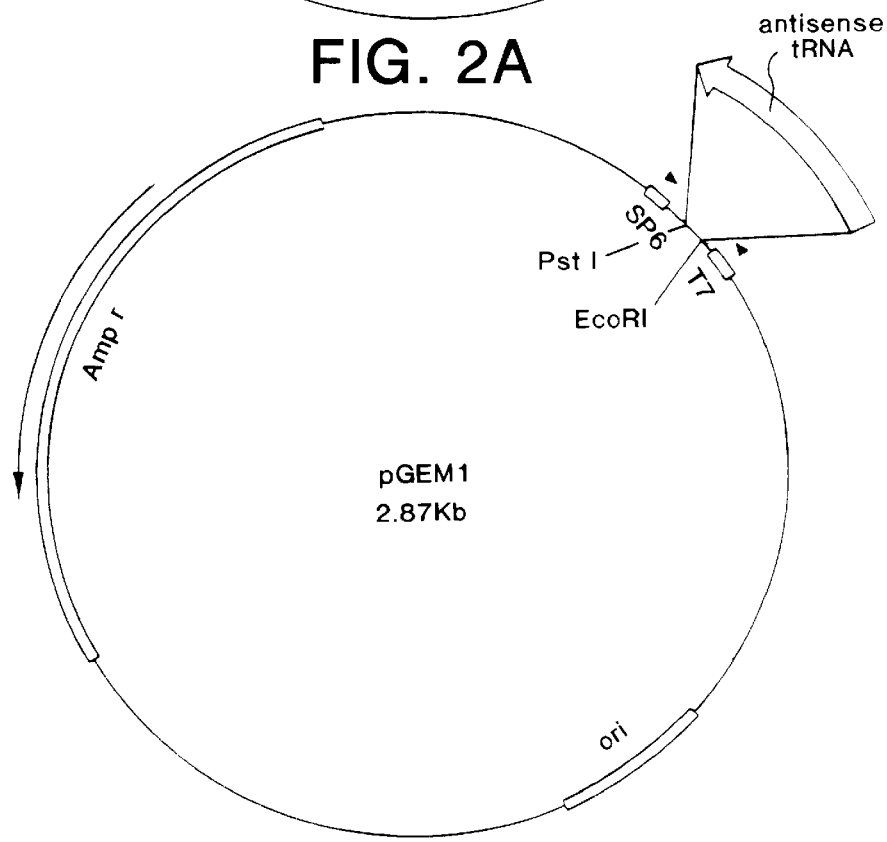

FIG. 2 shows the structures of plasmid vectors for antisense tRNAs. FIG. 2A shows the structure of the pV2M plasmid carrying an antisense tRNA gene under the λ Pr promoter. FIG. 2B shows the structure of the pGEM1 plasmid carrying an antisense tRNA under a T7 promoter.

FIGS. 3A, B, and C shows the growth curves of E. coli XL1-Blue transformed with pV2M-astRNA-Arg(AGA/G). Cells were grown in L-broth medium containing 50 µg/ml ampicillin. In 3A, the culture was grown at 30° C. and then divided into two halves at the point indicated by an arrow. One half was kept at 30° C. (♦), while the other was transferred to a 42° C. water bath (■) at the time point indicated by an arrow. In 3B, a part of the culture grown at 30° C. (♦) was shifted to 42° C. at the time points indicated by arrows 1 (■) and 2 (♦). In 3C, a part of the culture grown at 30° C. (■) was shifted to 42° C. (■) after 2 hr incubation indicated by arrow 1. Part of the 42° C. culture was transferred back to 30° C. (◇) at the time point indicated by arrow 2.

FIG. 4 shows the incorporation of $^{35}$S-Methionine and $^3$H-Thymidine after Temperature Shift. E. coli XL1-Blue harboring pV2M-astRNA-Arg(AGA/G) was grown at 30° C. in M9 medium supplemented with tryptophan (20 µg/ml), proline (20 µg/ml) and ampicillin (50 µg/ml). For $^{35}$S-methionine incorporation, an overnight culture was carried out in the presence of 10 µg/ml non-radioactive methionine. The overnight culture was diluted 10 fold with fresh M9 medium supplemented as described above. The diluted culture was incubated at 30° C. in the presence of 4 µg/ml non-radioactive methionine and 20 µCi/ml $^{35}$S-methionine. After 2 hr incubation, the culture was divided into two halves; one was kept at 30° C. (♦) and the other was shifted to a 42° C. incubator (■). FIG. 4A shows the relative cell growth after the temperature shift as measured by a Klett meter.

FIG. 4B shows the relative $^{35}$S-methionine incorporation into hot TCA-insoluble materials.

For $^3$H-thymidine incorporation, the procedure was the same as in 4A for $^{35}$S-methionine incorporation, except that the overnight culture contained 10 µg/ml thymidine and 5 µg/ml uracil, and that the culture contained 1 µg/ml thymidine, 5 µg/ml uracil, and 10 µCi $^3$H-thymidine. FIG. 4C shows the relative cell growth at 30° C. (♦) and 42° C. (■). FIG. 4D shows the relative [$^3$H] thymidine incorporation into cold TCA-insoluble materials.

FIG. 5 shows the growth curves of E. coli BL21(DE3) transformed pGEM1 harboring Various Antisense tRNA Genes in the Absence and the Presence of IPTG. Cells were grown at 37° C. in L-broth medium containing 50 µg/ml ampicillin. At the time point indicated by an arrow each culture was divided into two halves; one was incubated in the absence of IPTG (■) and the other in the presence of 1 mM IPTG (♦). FIG. 5A shows the growth curve of cells harboring the pGEM1 vector. FIG. 5B shows cells transformed with pGEM1-astRNA-Arg(AGA/G) for anti-tRN$_{AGA/G}^{Arg}$. FIG. 5C shows the growth curve of cells transformed with pGEM1-astRNA-Phe(UUU/C) for anti-tRNA$_{UUU/C}^{Phe}$. FIG. 5D shows the growth curve for cells transformed with pGEM1-antRNA-Met(AUG) for anti-tRNA$_{AUG}^{fMe}$.

FIG. 6 shows the effects of Anti-tRNA$_{AGA/G}^{Arg}$ on cellular tRNAs levels. tRNAs were detected by Northern blot hybridization with use of a $^{32}$P-labeled oligonucleotide complementary to tRNA$_{AGA/G}^{Arg}$ in FIG. 6A and to tRNA$_{UUU/C}^{Phe}$ in FIG. 6B. RNA extracts from *E. coli* XL1-Blue harboring the pV2M vector were applied to lanes 1 and 2, and those from cells harboring pV2M-astRNA-Arg (AGA/G) to lanes 3 and 4. The RNA extracts from cells incubated at 30° were applied to lanes 1 and 3 and those at 42° C. to lanes 2 and 4. The same cell extracts were applied to A and B. The position of tRNAs are indicated by arrow b. The band at position a indicates a new band that appeared after induction of anti-tRNA$_{AGA/G}^{Arg}$ at 42° C.

FIG. 7 shows the effects of anti-tRNA$_{AGA/G}^{Arg}$ induced by IPTG on cellular tRNAs. tRNA$^{Phe}$ and tRNA$^{Arg}$ were detected by RNase protection analysis. 5 μg of total cellular RNA was hybridized with $^{32}$P-labeled antisense probes. RNA extracted from *E. coli* BL21(DE3) harboring pGEM1-astRNA$_{AGA/G}^{Arg}$ (lanes 1 and 2) or pGEM1vector (lanes 3 and 4) was analyzed with anti-phenylalanine tRNA probe (lanes 1–4 in A) and with anti-arginine tRNA probe (lanes 1–4 in B). Cells were incubated with (lanes 2 and 4) and without (lanes 1 and 3) 1 mM IPTG for 2 hr before RNA extraction. After hybridization, the reaction mixture was treated with RNase A plus T1 according to the manual for RPAII™ Ribonuclease Protection assay kit (Ambion, Inc.). RNases were removed and the protected RNA probe was analyzed by polyacrylamide gel in 8M denaturing urea. The bands at a and b in A correspond to 38 and 33 to 34 base-pairs in length, respectively. The bands at a and b in B correspond to 39 and 34 to 35 base-pairs, respectively. Bands at position a have expected sizes on the basis of the size of the probe used. Bands at position b were probably a result of over-digestion of band a.

Figure 8A:
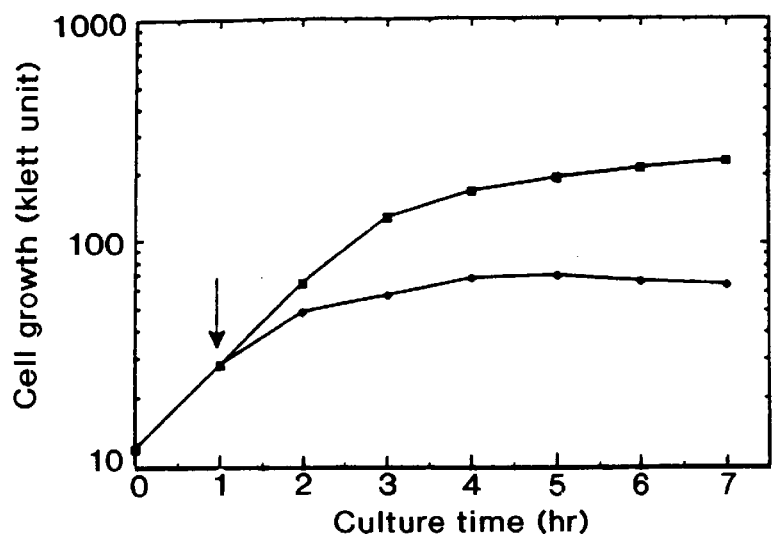
FIG. 8A, FIG. 8B, and FIG. 8C show the effects of Anti-$tRNA_{AGA/G}^{Arg}$ and Anti-anti-$tRNA_{AGA/G}^{Arg}$ on cell growth.
Figure 8B:
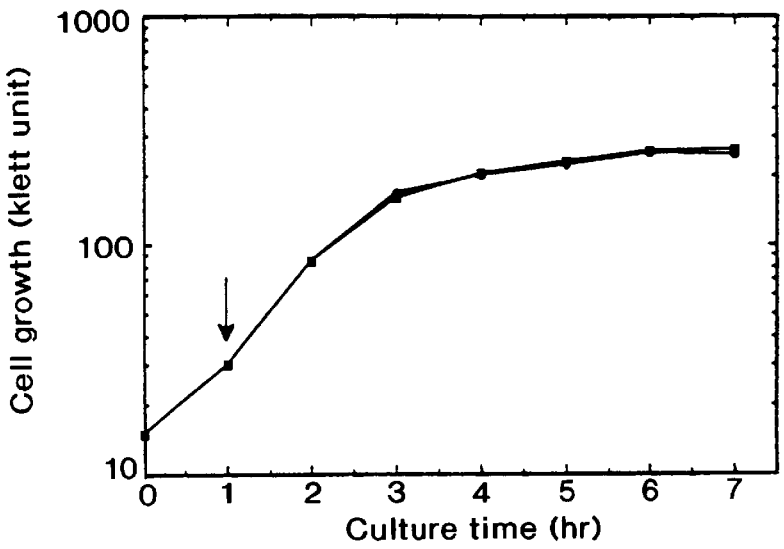
Figure 8C:
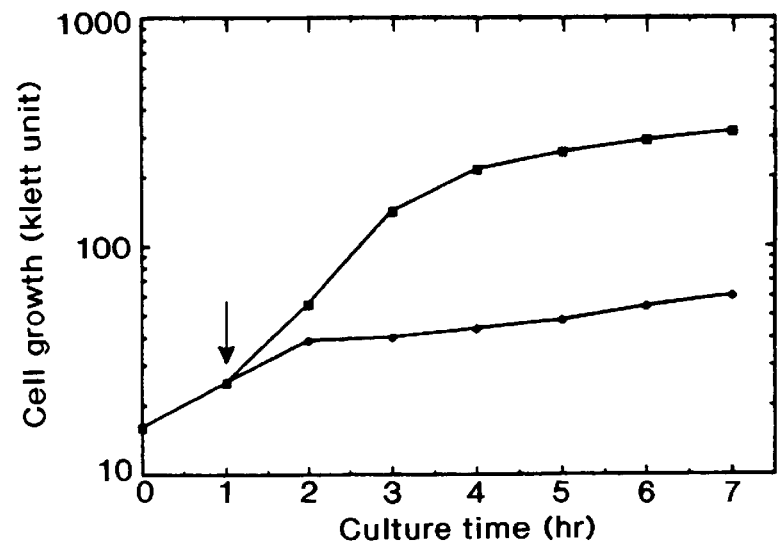

FIG. 8 shows the effects of Anti-tRNA$_{AGA/G}^{Arg}$ and Anti-anti-tRNA$_{AGA/G}^{Arg}$ on cell growth. FIG. 8A shows the growth curves for *E. coli* XL1-Blue harboring pGEM1-astRNA-Arg(AGA/G) grown at 37° C. in L-broth medium in the absence (■) and the presence of (♦) of 1 mM IPTG. FIG. 8B shows the growth curves for cells harboring both pGEM1-astRNA-Arg(AGA/G) and pGEM2-anti-astRNA-Arg(AGA/G). FIG. 8C shows the growth curves for cells harboring pGEM2-anti-astRNA-Arg(AGA/G). The cultures in FIGS. 8A, B, and C contained 50 μg/ml ampicillin, 50 μg/ml ampicillin plus 50 μg/ml kanamycin, and 50 μg/ml kanamycin, respectively. IPTG (1 mM) was added at the time point indicated by an arrow.

FIG. 9A shows the structure of antisense tRNA$^{met}$ and recombinant plasmids. Nucleotide sequence of wheat germ initiator tRNA$^{met}$ (light type) and antisense RNA (bold type). Three nucleotides at the 5'-end of antisense RNA belong to the EcoRV site.

FIG. 9B shows the synthesized DNA fragment, consisting of Sp6 promoter region, antisense RNA coding fragment and additional nucleotides to clone it into the BamHI site of plasmid DNA and generate EcoRV site.

FIG. 9C shows the structure of recombinant plasmids pAST and pGES used for in vitro transcription of antisense and sense RNA. pAST and pGES were linearized by EcoRV and HphI, respectively. Bold arrows indicate Sp6 and T7 promoter regions, light arrows represent direction of antisense and since RNA transcription. BamHI and sites shown in brackets were used for cloning of DNA oligonucleotide fragment.

FIG. 10 shows the stability of antisense tRNA$^{met}$ in wheat germ extract. Labeled antisense RNA was added to the in vitro wheat germ translation system without (□) or with 8 μM of non-labeled RNA (■) and 40 u of ribonuclease inhibitor (□). At different time points aliquotes of reaction mixture were spotted onto DE-81 filter and after washing radioactivity was measured using a liquid scintillation counter.

Figure 11A:
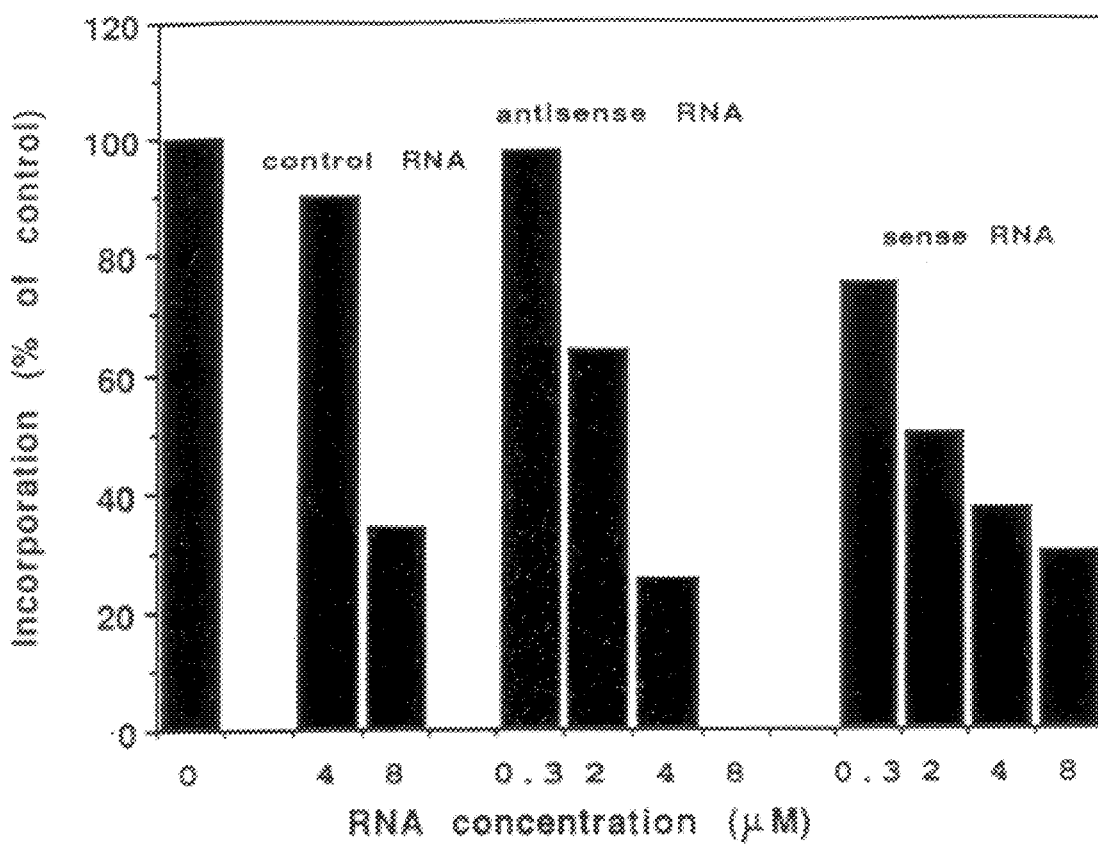
FIG. 11A and FIG. 11B show the inhibition of BMV and mRNA translation in vitro by antisense $tRNA^{met}$.
Figure 11B:
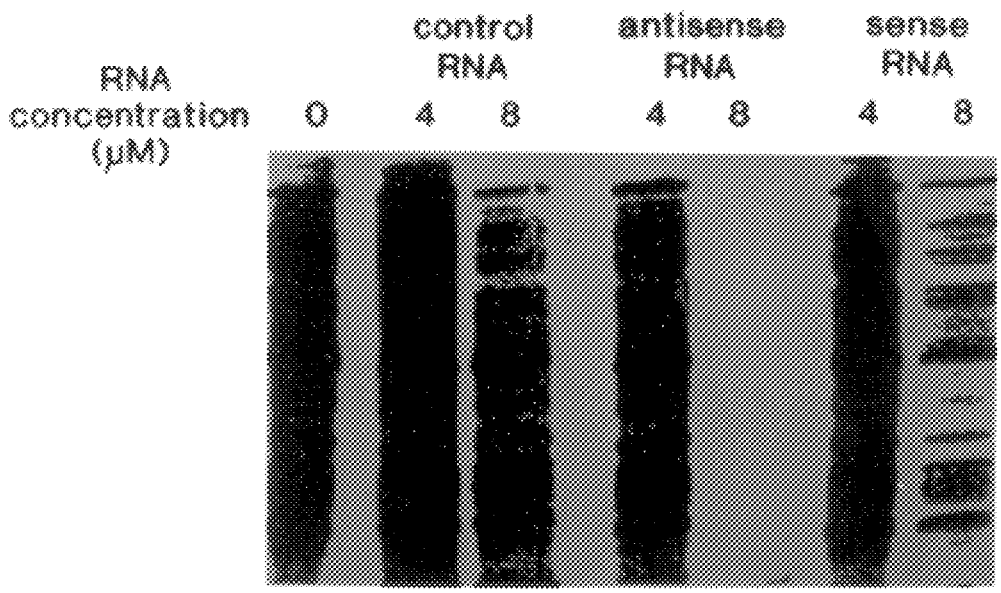

FIG. 11A shows the inhibition of BMV mRNA translation in vitro by antisense tRNA$^{met}$. A control antisense and sense RNA were added to the wheat germ extract at indicated concentrations. After preincubation in vitro translation was initiated by addition of reaction mixture containing mRNA BMV. After 60 minutes incubation, efficiency [$^{35}$S] methionine incorporation was measured as described in Materials and Methods.

FIG. 11B shows the analysis of proteins synthesized in wheat germ extract in the presence of different concentrations of control, antisense and sense RNA by SDS polyacrylamide gel electrophoresis.

Figure 12A:
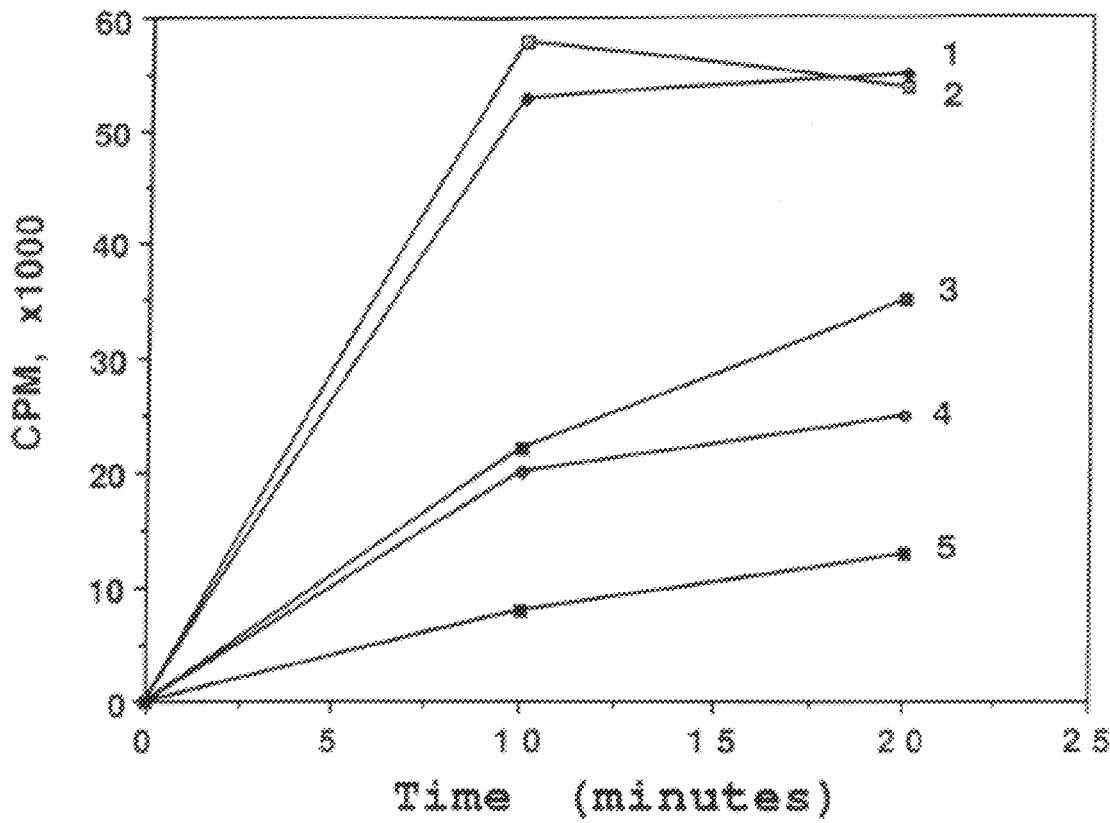
FIG. 12A shows the effect of control and antisense RNA on efficiency of in vitro translation at different incubation intervals.

FIG. 12A shows the effect of control and antisense RNA on efficiency of in vitro translation at different incubation intervals. In vitro translation of BMV mRNA was conducted without addition of RNA (curve 1) and in the presence of different concentrations of control RNA (curve 2—2 μM, curve 4—6 μM) or antisense RNA (curve 3—2 μM, curve 5—6 μM). Aliquotes of reaction mixtures were taken at different time points and incorporated radioactivity was checked.

Figure 12B:
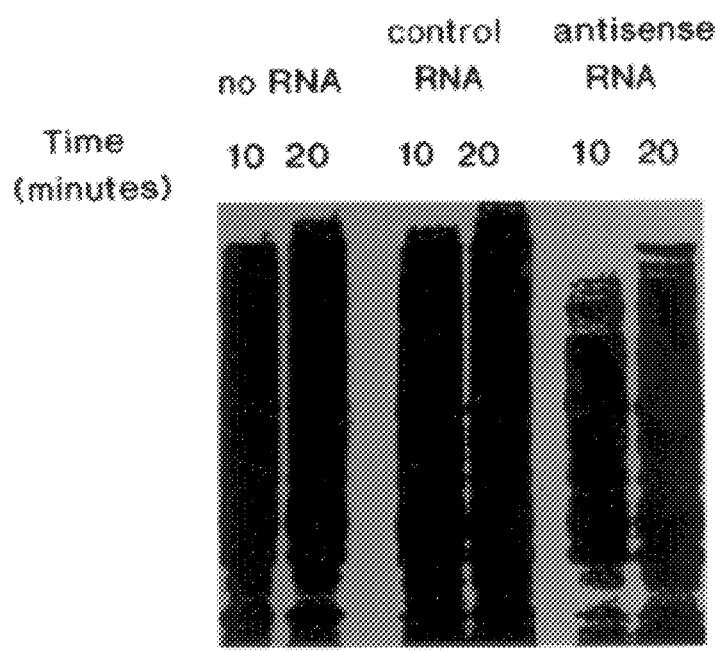
FIG. 12B shows the analysis of protein patterns synthesized in vitro without or in the presence of control and antisense RNA.

FIG. 12B shows the analysis of protein patterns synthesized in vitro without or in the presence of control and antisense RNA at the indicated time points by SDS polyacrylamide gel electrophoresis.

FIG. 13A shows the detection of antisense RNA-tRNA$^{met}$ complex in wheat germ extract. In vitro labelled antisense RNA was added to the wheat germ extract and pre-incubated as indicated with or without competitive and non-competitive oligonucleotides 15 minutes at 4° C. and 15 minutes at 37° C. Probes were then analyzed on a native polyacrylamide gel. Lane 1 represents labeled antisense RNA probe.

FIG. 13B shows the resistance of antisense NA-tRNA$^{met}$ complex to the RNAaseA-T1 mixture. After incubation of labeled antisense RNA in wheat germ extract, probes were treated by RNAseA-T1 mixture at indicated dilutions of standard solution from Ambion, Inc. RPAII™ kit at 37° C.

FIG. 13C shows the hybridization analysis of antisense RNA-tRNA$^{met}$ complex using labeled oligonucleotide, complementary to the first loop from the 3'-end of tRNA$^{met}$. Lanes 1 and 2 correspond to lanes 2 and 3 from panel B. Lanes 3 and 4 represent probe from reaction mixtures incubated in presence of non-labeled antisense RNA. After electrophoresis part of the gel, containing these samples were blotted to the nylon N and hybridized. Bold arrows at all panels show the position of antisense RNA-tRNA$^{met}$ complex, light arrows correspond to the position of antisense RNA.

FIG. 14 shows the influence of additional tRNA on the inhibition of BMV mRNA translation in wheat germ extract by antisense RNA. A wheat germ tRNA fraction was added into the in vitro translation mixture at the indicated quantities. The reaction was conducted without RNA or with control (3 μM) antisense (3 μM) or sense (5 μM) RNA. Probes of reaction mixture after 1 hour incubation were processed as described in Materials and Methods.

These studies show the inhibition of protein synthesis by inhibition of RNA translation by antisense RNA.

MATERIALS AND METHODS

[γ-$^{32}$P]ATP, $^{35}$S-methionine and $^{3}$H-methy thymidine were purchased from Amersham or ICN. Restriction enzymes were from New England BioLabs or Bethesda Research Laboratories.

Bacterial Strains and Plasmids E. coli XL-Blue (Bullock, 1987) and BL21(DE3) (Studier and Moffatt, 1988) were used. Cells were grown in L-broth medium (Miller, 1972). pV2M (Queen, 1983), pGEM1 or pGEM2 (Promega) were used for expression of antisense or anti-antisense tRNAs.

Construction of Plasmids

Oligonucleotide corresponding to the target sequences shown in FIG. 1 were synthesized. At the 5' end of the antisense gene (for example, corresponding to the 39th base for tRNA$_{AGA/G}^{Arg}$) extra 5 bases (AATTC) were added to create an EcoRI site, and at the 3' end (corresponding to the 5' end of tRNA) extra 5 bases (CTGCA) were added to create a PstI site. For the construction of pV2M-astRNA-Arg(AGA/G), the synthetic oligonucleotide was first inserted between the unique EcoRI and PstI sites of PGFIBI (Normandy et al., 1986). The 99-bp EcoRI-Hind III fragment was then purified and inserted between the EcoRI and Hind III sites of pV2M (see FIG. 2A) which are downstream of the Pr promoter. The transcript from the Pr promoter thus consists of AATTC sequence at the 5' end followed by the 39-base antisense RNA complementary to the 5'-end half of tRNA$_{AGA/G}^{Arg}$ (see FIG. 1A) and a 55-base sequence at the 3' end. The 55-base sequence is derived from the 3'-end transcriptional termination signal from the vector, and composed of 5'TGCAGCATGAAATCATCCTTAGC-GAAAGCTAAGGATTTTTTTATCTGAAATCGA3' (Seq. ID No.6).

In order to express antisense tRNAs under a T7 promoter in pGEM1 (see FIG. 2B), the synthetic oligonucleotide described above was directly inserted between the EcoRI and PstI sites. For anti-tRNA$_{UUU/C}^{Phe}$ and anti-tRNA$_{AUG}^{fMet}$ extra 4 bases (TGCA) were added at the 3' end of the antisense tRNA gene to create a PstI site. The transcripts thus produced under the T7 promoter contained 14 extra bases at the 5' end followed by the RNA sequence complementary to the 5'-end half of tRNA (boxed sequences in FIG. 1). Since there is no well-defined transcriptional termination signal in this vector, the exact structure of the 3' end of the antisense RNA has not been determined. The resultant plasmids were designated PGEM1-astRNA-Arg (AGA/G), pGEM1-astRNA-Met(AUG) and pGEM1-astRNA-Phe(UUU/C) for anti-tRNA$_{AGA/G}^{Arg}$, anti-tRNA$_{AUG}^{fMe}$ and anti-tRNA$_{UUU/C}^{Phe}$, respectively. In order to express the 5'-end half of tRNA$_{AGA/G}^{Arg}$ (FIG. 1A) in the right or sense (anti-anti) orientation, the same oligonucleotide used for the construction of pGEM1-astRNA-Arg (AGA/G) was directly inserted between the EcoRI and PstI sites of PGEM2. Subsequently, the amp' marker was disrupted by inserting the Tn5-kanamycin-resistant (kan') gene as from pTH3 (Musso et al., 1989). The kan' gene was obtained by SmaI digestion and inserted into the ScaI site in the amp' gene of pGEM2-anti-astRNA-Arg(AGA/G). The resulting plasmid was designated pGEM2-anti-astRNA-Arg (AGA/G).

Protein and DNA Synthesis

E. coli XL1-Blue carrying pV2M-astRNA-Arg(AGA/G) was grown in M9 medium (Maniatis et al., 1983) supplemented with 50 µg/ml ampicillin. Labeling experiments with $^{35}$S-methionine and $^{3}$H-thymidine were carried out according to the method described by Inouye, (1969). For labeling with $^{35}$S-methionine, 4 µCi/ml non-radioactive methionine and 20 µCi/ml $^{35}$S-methionine were added in the medium. For the experiments with $^{3}$H-thymidine, 10 µCi/ml $^{3}$H-thymidine, 1 µg/ml non-radioactive thymidine and 5 µg/ml uracil were added in the medium. For $^{35}$S-methionine incorporation, the filters were treated for 30 min in a boiling water bath to remove the radioactivity incorporated into the tRNA fractions.

Detection of tRNAs tRNA fraction was prepared as described previously (Witter, et al., 1986). Northern blot analysis was carried out according to the method described by Kroczek and Siebert (1990). tRNAs were also detected by the ribonuclease protection assay (Ambion, Inc.).

Plasmid Construction and in vitro RNA synthesis

Plasmids for the expression of antisense or sense RNA were constructed with pUC19 (11). pAST for antisense tRNA was constructed by inserting the synthetic oligonucleotides shown in 6B between the BamHI and SmaI sites of pUC19. The resulting plasmid has the antisense RNA coding region under the Sp6 promoter as shown in FIG. 9C. pGES for sense RNA was constructed. The same synthetic oligonucleotide (FIG. 9B) was inserted between the BamHI and HincII sites of pGEM2 (Promega; FIG. 9B). Antisense RNA was produced in vitro by transcribing pAST DNA linearized by EcoR5 with use of Sp6 RNA polymerase. Sense and control RNAs were prepared with T7 and Sp6 RNA polymerases using pGES and pGEM2 DNA linearized by Hph1 and EcoRI, BamH1 and Sma1, respectively. The in vitro RNA production was carried out with the Promega kit according to the manufacturer's instructions. Purification of RNA was performed with a Qiagen-tip 20 column (Qiagen Inc.). The final RNA preparation was dissolved in water and the RNA concentration was spectrophotometrically determined.

In vitro Translation of BMV RNA

BMV mRNA for in vitro translation was purchased from Promega. Wheat-germ extract was obtained from Amersham, Inc. Cell-free protein synthesis was performed according to the supplier's instruction unless otherwise indicated. Antisense, sense and control RNA were added to 7.4 µl of the wheat germ extract and the mixtures were pre-incubated at 4° C. for 15 minutes and than at 37° C. for 15 minutes. The reaction was initiated by adding a solution containing 25 µCi of [$^{35}$S] methionine (1,000 mCi/mmole; Amersham) and 0.2 µg of BMV mRNA to the pre-incubated cell-free system. The final reaction volume was 15 µl. At the end of the reaction 2 µl of the reaction mixture was removed to determine the total level of protein synthesis. Proteins synthesized were separated by 12.5% SDS-polyacrylamide gel electrophoresis using the buffer system of Laemmli ( ) after electrophoresis gels were dried for autoradiography.

In order to examine RNA degradation during in vitro translation, RNA labeled with [α-$^{32}$P]CTP was added to the reaction mixture. After incubation the reaction mixtures were spotted onto a DE-81 chromatography paper (Whatman), which was washed extensively in 5% dibasic sodium phosphate. The radioactivity remaining on the paper was then measured.

RNase Protection Assay

For quantitation of tRNA$^{met}$ in the wheat germ extract, labeled antisense RNA was added to the purified tRNA fraction from the extract. Then samples were processed using the Ambion, Inc. RPAII™ kit.

Detection of Antisense RNA-tRNA$^{met}$ Complex $^{32}$P-labeled antisense RNA was added to the in vitro translation system with or without preincubation in the presence of the wheat germ extract. At the end of the reaction the mixtures were fractionated by electrophoresis on an 12% non-denaturing polyacrylamide gel. The gel was then dried for autoradiography. For detecting the presence of tRNA in the complex with antisense RNA the same procedure was carried out with non-radioactive antisense RNA, and after electrophoresis, the gel was blotted using PosiBlot™ system (Stratagene) to the Hybond™ N Nylon membrane (Amersham). The membrane was hybridized with a [$\alpha^{32}$P] labeled-oligonucleotide probe (5'-CCAGGTTTCGAATCCTGGGAC-3')(Seq. ID No. 7) which was complementary to the 3'-end region of tRNA$^{met}$. Hybridization and washing conditions were as previously described.

The invention described shows that in vitro translation of BMV mRNA in wheat germ extract can be effectively inhibited by antisense RNA targeted against a stable and abundant RNA such a tRNA$^{met}$. All these results establish that in the reaction mixture, antisense RNA formed a complex with its tRNA target.

With respect to concentrations, an excess of over tRNAs is best for maximal inhibition. In vitro translation was inhibited 100% (at 8 µM). With lower concentrations, control RNA revealed only non-specific inhibition.

An interesting finding in this work is that sense RNA has some effect most likely due to the interaction with the opposite strand of the tRNA molecule, which has several complementary nucleotides. Specificity of inhibition and complex formation was proven by simultaneous addition of a competitive oligonucleotide or additional wheat germ fraction.

Several other experiments have shown that RNA or oligideoxyribonucleotides were capable of inhibiting gene expression, even when their target had a significant RNA secondary structure, for example, TAR element of HIV virus, and double-stranded hairpin segments at the 5'-untranslated region of SV40 mRNA.

It is considered, that it may not be necessary for the whole target RNA molecule to be single-stranded for the efficient binding and inhibition of RNA function, but only that there be a spontaneous unfolding of a small portion of the molecule for a certain time.

It was found in accordance with the invention that at a working concentration of antisense tRNA most of the tRNA$^{met}$ molecules are in a stable complex, which prevent tRNA from performing its normal function. On the other hand, there is available data investigating binding of tRNA to a linear RNA, containing a complementary triplet. It was shown that a complex can be detected, formed by tRNA and a sequence complementary to the anticodon under the condition where no complex has been detected by a pair of complementary triribonucloetides.

Stability of the complex between anticodon loop and a complementary linear RNA is much higher than expected from interaction of two linear RNAs.

The findings in connection with the invention are that antisense RNA can interact with two loops, both of them contain 7 non-complexed nucleotides, including the anticodon. Such kinds of interaction can be quite efficient.

The invention shows the antisense RNA approach to inhibit a cells growth by using tRNA as a target in vivo. tRNA$^{met}$ is one, if not the most abundant RNA in living cells. By selecting as a target less abundant or even minor tRNA, it is contemplated that protein synthesis in cancer cells or cells infected by viruses be inhibited or even stopped. Another application is to use as a target tRNA that participates in the replication cycle of viruses, for example tRNA$^{trp}$, which primes DNA synthesis of avian sarcoma and leukosis viruses or tRNA$^{lys}$, which participates in the replication of HIV viruses. Another possible target of antisense tRNA may be nonsense suppressor tRNA; its concentration in cells is very low. Apparently, they have a very specific cellular function and changes in its concentration can influence the regulation of gene expression.

Thus, it is within the scope of the invention to select one or more of any of the tRNAs as a target, construct an appropriate complementary antisense RNA to the tRNA, (to less than the entire tRNA), thus forming the complex antisense RNA and the tRNA for inhibition (non-specific) of translation of the mRNA. This fundamental invention offers numerous practical utilities described herein and others that will become apparent to one skilled in the art.

The methodology for making the constructs used in the invention and other techniques are known to one skilled in the art. See for instance, Molecular Cloning, Second Ed. Vols. 1–3 (1990) Sambrook et al., Cold Spring Harbor Laboratory Press; A Practical Guide to Molecular Cloning, Second Ed., (1988), Bernard Perbal, John Wiley & Sons; and Current Protocols in Molecular Biology, Vols. 1 and 2, (1987), Ausubel et al., Greene Publishing Associates and Wiley-Interscience.

In accordance with the invention, a tRNA will be selected a dsDNA oligonucleotides sequence synthesized which is complementary to a sequence of the target tRNA. The double stranded fragment encoding the antisense RNA is cloned into a vector such as to become under the control of an inducible promoter. A selected organism is transformed or transfected with the plasmid containing the synthetic DNA which when the RNA is expressed, the RNA is capable of annealing to the target tRNA, inhibiting translation and thus the growth of the organism.

REFERENCES

1. Takayama, K. M. et al., *Crit. Rev. Biochem* 25, 155–184 (1990).
2. Ikemura, T., *J. Mol. Biol.* 151, 389–409 (1981).
3. Garcia, G. M. et al., *Cell* 45, 453–459 (1986).
4. Egan, B. Z. et al., *Biochem. Biophys. Res. Comm.* 55, 320–327 (1973).
5. Barrell, B. G. et al., *FEBS Letters* 3, 275–278 (1969).
6. Queen, C. J., *Mol. & Appl. Gen.* 2, 1–10 (1983).
7. Studier, F. et al., *J. Mol. Biol.* 189, 113–130 (1986).
8. Bullock, W. *Biotechnology* 5, 376–393 (1987).
9. Helene, C. et al., *Biochem. Biophys. Acta.* 1049, 99–125 (1990).
10. van der Krol, A. R., et al., *Biotechniques* 6, 958–976 (1988).
11. Green, P. J. et al., *Ann. Rev. Biochem.* 55, 569–597 (1986).
12. Hirashima, A., et al. *J. Biochem.* 106, 163–169 (1989).
13. Anfossi, G. et al., *Proc. Natl. Acad. Sci.* 86, 3379–3383 (1989).
14. Jaskulski, D., et al., *Science* 240, 1544–1546 (1988).
15. Buck, H. M., et al., *Science* 248, 208–212 (1990).
16. Agris, C. H. et al., *Biochemistry* 25, 6268–6275 (1986).
17. Smith, C. C. et al., *Proc. Natl. Acad. Sci. USA* 83, 2787–2791 (1986).
18. Zerial, A., et al., *Nucleic Acids Res.* 15, 9909–9919 (1987).
19. Yanisch-Perron, C. et al., *Gene* 33, 103–119 (1985).
20. Laemmli, U. K., *Nature* 227, 680–685 (1970).
21. Zeff, R. A., et al., *J. Immunol.* 137, 897 (1986).
22. Walder, J., *Genes Dev.* 2, 502–504 (1986).
23. Vickers, T., et al., *Nucleic Acids Res.* 19, 3359–3368 (1991).
24. Graessman, M. et al., *Nucleic Acids Res.* 19, 53–39 (1991).

25. Yoon et al., *J. Mol. Biol.* 99, 507–511 (1975).
26. Chastain, M. et al., *Nucleic Acids Res.* and *Mol. Bio.* (Cohn, W. E., Moldave, K. eds.) 131–177 (Florida Academic Press in progress).
27. Daznell, J., *Mol. Cell Biol.* 136–138.
28. Aiyar, A. et al., *J. Virol.* 66, 2464–2472 (1992).
29. Barat, C. et al., *Nucleic Acids Res.* 19, 751–757 (1991).
30. Hatfield, D., *Trends Biochem. Sci.* 10, 201–204 (1985).
31. Mary Ann Liebert, Inc. Publishers, "Antisense, Research and Development", Vol. 1, No. 2, (summer 1991),
32. Inouye, M., *Gene* 72, 25–34 (1988).
33. Inouye, M., *J. Bacteriology.* 99:842–850 (1969).
34. Kiesewetter, S. et al., *Nuc. Acid Res.* 15, 3184–3184 (1987).
35. Kroczek, R. A. and Siebert E., *Anal. Biochem.* 184, 90–95 (1990).
36. Maniatis, T. et al., Molecular Cloning. A Laboratory Manual. Cold Spring Harbor, N.Y., Cold Spring Harbor Laboratory Press (1982).
37. Miller, J. H., ed, Experiments in molecular genetics. Cold Spring Harbor Laboratory, Cold Spring Harbor, N.Y. (1972).
38. Musso, R. E. and Hodam, T., *Gene* 85, 205–207 (1989).
39. Sprinzl, M. et al., *Nuc. Acid Res.* 17 (Supplement) r1–r172 (1989).
40. Varmus, H. and Swanstrom, R., Replication of retroviruses pp. 75–134 in RNA Tumor Viruses (2nd edition). Cold Spring Harbor Laboratory, Cold Spring Harbor, N.Y. (1985).
41. Witter, A. J. and Stadtman, T. C., *Archives of Biochem. and Biophy.* 248, 540–550 (1986).

We claim:

1. A method for controlling the synthesis of a protein in a bacterium or in a cell free system, which comprises obtaining an antisense RNA construct which anneals to a portion of a target tRNA, and causing the antisense RNA construct to anneal to complementary bases of the target tRNA to form an antisense RNA-tRNA complex, thereby inhibiting translation of the protein.

2. The method of claim 1, wherein the antisense RNA is complementary to the 5'-half of the tRNA including its anticodon.

3. The method of claim 1, wherein the inhibition is of viral protein translation.

4. The method of claim 3, which is in vitro.

5. The method of claim 4, wherein the translation is inhibited in a cell-free system.

6. The method of claim 3, wherein the virus is BMV.

7. The method of claim 1, which causes inhibition of the growth of a bacterium.

8. The method of claim 7 which is in vivo.

9. The method of claim 8, wherein the bacterium is E. coli.

10. The method of claim 1, wherein the antisense RNA is complementary to the portion of the tRNA from the 5' end of the tRNA to the 3' end of the stem and loop structure which is nearest the 5' end of the tRNA.

11. The method of claim 1 wherein the portion of the tRNA to which the antisense construct anneals has little secondary structure.

12. A synthetic antisense RNA-tRNA complex of an antisense RNA annealed to complementary bases of a target tRNA, which complex inhibits protein translation.

13. The antisense RNA-tRNA complex of claim 12, wherein the antisense RNA is complementary to the 5'-half of the tRNA including its anticodon.

14. The antisense RNA-tRNA complex of claim 12, wherein the antisense RNA is complementary to the portion of the tRNA from the 5' end of the tRNA to the 3' end of the stem and loop structure which is nearest the 5' end of the tRNA.

15. The antisense RNA-tRNA complex of claim 12 wherein the portion of the tRNA to which the antisense construct anneals has little secondary structure. 5' end of the tRNA.

16. The antisense RNA-tRNA complex of claim 15 wherein the 3' and 5' ends of the antisense construct are single stranded.

17. A bacterium transformed with a recombinant plasmid harboring a gene encoding an antisense RNA molecule which anneals to a target tRNA, thereby forming an antisense RNA-tRNA complex, which complex inhibits translation.

18. The bacterium of claim 17, wherein the bacterium is E. coli.

19. The bacterium of claim 17, wherein transcription of the gene encoding the antisense RNA is under the control of an inducible promoter.

20. The bacterium of claim 19 wherein the inducible promoter is the lac, $\lambda P_r$, T7, or Sp6 promoter.

21. The bacterium of claim 19, wherein antisense RNA transcription by the promoter is induced at a temperature of about 42° C.

22. A synthetic DNA molecule coding for an antisense RNA, which antisense RNA anneals to complementary bases of a portion of a target tRNA less than the entire target tRNA, where by protein translation is inhibited.

23. The synthetic DNA molecule of claim 22 wherein the antisense RNA anneals to the 5'-half of the tRNA including its anticodon.

24. The synthetic DNA molecule of claim 23, wherein the DNA molecule is linked to an inducible promoter such that transcription of the DNA molecule is under the control of the inducible promoter.

25. The synthetic DNA molecule of claim 22, which encodes an antisense RNA which anneals to arginyl tRNA, formyl methionyl tRNA or phenylalanyl tRNA.

26. A recombinant plasmid comprising a replicable vector and a gene encoding an antisense RNA molecule which anneals to a target tRNA, thereby forming an antisense RNA-tRNA complex, which complex inhibits protein translation.

27. The plasmid of claim 26 wherein the vector is selected from the group consisting of pV2M, pGEM1, pGEM2, pAST, pGES, and pUC19.

28. The plasmid of claim 26, wherein transcription of the gene encoding the antisense RNA is under the control of an inducible promoter.

29. The plasmid of claim 28 wherein the inducible promoter is the lac $\lambda P_r$, T7, or Sp6promoter.

30. The plasmid of claim 28, wherein antisense transcription by the promoter is induced at a temperature of about 42° C.

31. A method for controlling the function of a tRNA in a bacterium or a cell free system comprising permitting an antisense molecule which anneals to a tRNA to anneal to a portion of the tRNA, which portion includes either the 5' end or the 3' and and at least one stem and loop structure of the tRNA thereby inhibiting the function of the tRNA.

32. The method of claim 29 wherein the portion of the tRNA comprises the 5' end of the tRNA to the 3' end of the stem and loop structure which is nearest the 5' end of the tRNA.

33. The method of claim 30 wherein the portion further comprises the 3' end of the stem and loop structure nearest the 5' end of the tRNA to the 3' end of the anticodon of the tRNA.

34. The method of claim 29 wherein the portion comprises either the 5' or 3' end of the tRNA up to and including the anticodon.

35. The method of claim 29 wherein the tRNA is selected from the group consisting of arginyl tRNA, formyl methionyl tRNA and phenylalanyl tRNA.

36. A method for controlling growth of a bacterium comprising selecting a tRNA of the bacterium as a target, synthesizing a DNA oligonucleotide sequence which is complementary to a sequence of the target tRNA, which sequence of the target tRNA is less than the entire tRNA, cloning the DNA sequence into a vector to form a recombinant plasmid wherein expression of the DNA sequence is under the control of an inducible promoter, transforming the bacterium with the recombinant plasmid, providing the condition under which the promoter promotes expression of the DNA sequence to form an RNA which anneals to the target tRNA, and permitting the RNA to anneal to the target tRNA, thereby inhibiting translation and the growth of the bacterium.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 77 base pairs
        ( B ) TYPE: nucleic acid
        ( C ) STRANDEDNESS: unknown
        ( D ) TOPOLOGY: unknown ( i i ) MOLECULE TYPE: tRNA ( i i i ) HYPOTHETICAL: NO ( i v ) ANTI-SENSE: NO ( v ) FRAGMENT TYPE: C-terminal ( v i ) ORIGINAL SOURCE:
        ( A ) ORGANISM: Escherichia coli ( x i ) SEQUENCE DESCRIPTION: SEQ ID NO:1:

```
GCGCCCUUAG  CUCAGUUGGA  UAGAGCAACG  ACCUUCUAAG  UCGUGGGCCG  CAGGUUCGAA      60

UCCUGCAGGG  CGCGCCA                                                         77
```

( 2 ) INFORMATION FOR SEQ ID NO:2:

( i ) SEQUENCE CHARACTERISTICS:
        ( A ) LENGTH: 77 base pairs
        ( B ) TYPE: nucleic acid
        ( C ) STRANDEDNESS: both
        ( D ) TOPOLOGY: linear ( i i ) MOLECULE TYPE: tRNA ( i i i ) HYPOTHETICAL: NO ( i v ) ANTI-SENSE: NO ( v ) FRAGMENT TYPE: C-terminal ( v i ) ORIGINAL SOURCE:
        ( A ) ORGANISM: Escherichia coli ( x i ) SEQUENCE DESCRIPTION: SEQ ID NO:2:

```
CGCGGGGUGG  AGCAGCCUGG  UAGCUCGUCG  GGCUCAUAAC  CCGAAGAUCG  UCGGUUCAAA      60

UCCGGCCCCC  GCAACCA                                                         77
```

( 2 ) INFORMATION FOR SEQ ID NO:3:

( i ) SEQUENCE CHARACTERISTICS:
    ( A ) LENGTH: 76 base pairs
    ( B ) TYPE: nucleic acid
    ( C ) STRANDEDNESS: both
    ( D ) TOPOLOGY: both ( i i ) MOLECULE TYPE: tRNA ( i i i ) HYPOTHETICAL: NO ( i v ) ANTI-SENSE: NO ( v ) FRAGMENT TYPE: C-terminal ( v i ) ORIGINAL SOURCE:
    ( A ) ORGANISM: Escherichia coli ( x i ) SEQUENCE DESCRIPTION: SEQ ID NO:3:

```
GCCCGGAUAG  CUCAGUCGGU  AGAGCAGGGG  AUUGAAAAUC  CCCGUGUCCU  UGGUUCGAUU        60

CCGAGUCCGG  GCACCA                                                           76
```

( 2 ) INFORMATION FOR SEQ ID NO:4:

( i ) SEQUENCE CHARACTERISTICS:
    ( A ) LENGTH: 114 base pairs
    ( B ) TYPE: nucleic acid
    ( C ) STRANDEDNESS: both
    ( D ) TOPOLOGY: unknown ( i i ) MOLECULE TYPE: tRNA ( i i i ) HYPOTHETICAL: NO ( i v ) ANTI-SENSE: NO ( v ) FRAGMENT TYPE: C-terminal ( v i ) ORIGINAL SOURCE:
    ( A ) ORGANISM: Escherichia coli ( x i ) SEQUENCE DESCRIPTION: SEQ ID NO:4:

```
AUCAGAGUGG  CGCAGCGGAA  GCGUGGUGGG  CCCAUAACCC  ACAGGUCCCA  GGAUCGAAAC        60

CUGGCUCUGA  UACCAGGAUA  UGGGCCCACC  ACGCUUCCGC  UGCGCCACUC  UGAU            114
```

( 2 ) INFORMATION FOR SEQ ID NO:5:

( i ) SEQUENCE CHARACTERISTICS:
    ( A ) LENGTH: 63 base pairs
    ( B ) TYPE: nucleic acid
    ( C ) STRANDEDNESS: double
    ( D ) TOPOLOGY: linear ( i i i ) HYPOTHETICAL: NO ( i v ) ANTI-SENSE: NO ( v ) FRAGMENT TYPE: C-terminal ( v i ) ORIGINAL SOURCE:
    ( A ) ORGANISM: Escherichia coli ( x i ) SEQUENCE DESCRIPTION: SEQ ID NO:5:

```
GATCATTTAG  GTGACACTAT  AGAATATGGG  CCCACCACGC  TTCCGCTGCG  CCACTCTGAT        60

ATC                                                                          63
```

( 2 ) INFORMATION FOR SEQ ID NO:6:

( i ) SEQUENCE CHARACTERISTICS:

(A) LENGTH: 55 base pairs
(B) TYPE: nucleic acid
(C) STRANDEDNESS: unknown
(D) TOPOLOGY: unknown (xi) SEQUENCE DESCRIPTION: SEQ ID NO:6:

TGCAGCATGA AATCATCCTT AGCGAAAGCT AAGGATTTTT TTTATCTGAA ATCGA    55

(2) INFORMATION FOR SEQ ID NO:7:

(i) SEQUENCE CHARACTERISTICS:
(A) LENGTH: 21 base pairs
(B) TYPE: nucleic acid
(C) STRANDEDNESS: single
(D) TOPOLOGY: unknown (xi) SEQUENCE DESCRIPTION: SEQ ID NO:7:

CCAGGTTTCG AATCCTGGGA C    21